United States Patent
Jeong

(10) Patent No.: US 10,639,351 B2
(45) Date of Patent: May 5, 2020

(54) METHOD FOR TREATING AMYOTROPHIC LATERAL SCLEROSIS WITH A POLYNUCLEOTIDE ENCODING TWO OR MORE ISOFORMS OF HEPATOCYTE GROWTH FACTOR

(71) Applicant: Helixmith Co., Ltd., Seoul (KR)

(72) Inventor: Jae Gyun Jeong, Seoul (KR)

(73) Assignee: Helixmith Co., Ltd., Seoul (KR)

(*) Notice: Subject to any disclaimer, the term of this patent is extended or adjusted under 35 U.S.C. 154(b) by 380 days.

(21) Appl. No.: 15/030,999

(22) PCT Filed: Oct. 22, 2014

(86) PCT No.: PCT/KR2014/009971
§ 371 (c)(1),
(2) Date: Apr. 21, 2016

(87) PCT Pub. No.: WO2015/060650
PCT Pub. Date: Apr. 30, 2015

(65) Prior Publication Data
US 2016/0250291 A1 Sep. 1, 2016

(30) Foreign Application Priority Data

Oct. 22, 2013 (KR) .................. 10-2013-0126216
Oct. 22, 2014 (KR) .................. 10-2014-0143377

(51) Int. Cl.
*A61K 38/18* (2006.01)
*C07K 14/475* (2006.01)

(52) U.S. Cl.
CPC ...... *A61K 38/1833* (2013.01); *C07K 14/4753* (2013.01)

(58) Field of Classification Search
None
See application file for complete search history.

(56) References Cited

U.S. PATENT DOCUMENTS

| 5,328,836 | A | 7/1994 | Shima et al. |
| 5,500,354 | A | 3/1996 | Kitamura et al. |
| 5,580,859 | A | 12/1996 | Felgner et al. |
| 5,587,359 | A | 12/1996 | Higashio et al. |
| 5,652,225 | A | 7/1997 | Isner |
| 5,693,622 | A | 12/1997 | Wolff et al. |
| 5,830,879 | A | 11/1998 | Isner |
| 6,013,624 | A | 1/2000 | Goldberg et al. |
| 6,121,246 | A | 9/2000 | Isner |
| 6,143,714 | A | 11/2000 | Wong et al. |
| 6,248,722 | B1 | 6/2001 | Morishita et al. |
| 6,258,787 | B1 | 7/2001 | Isner |
| 6,316,419 | B1 | 11/2001 | Leiden et al. |
| 6,413,942 | B1 | 7/2002 | Feigner et al. |
| 6,498,144 | B1 | 12/2002 | Goldberg et al. |
| 6,699,837 | B2 | 3/2004 | Nakamura |
| 6,706,694 | B1 | 3/2004 | Wolff et al. |
| 6,887,477 | B1 | 5/2005 | Nagano et al. |
| 7,276,359 | B1 | 10/2007 | Musunuri et al. |
| 7,285,540 | B2 | 10/2007 | Morishita et al. |
| 7,323,297 | B1 | 1/2008 | Szoka et al. |
| 7,473,425 | B2 | 1/2009 | Fukuda |
| 7,745,174 | B2 | 6/2010 | Kim et al. |
| 7,812,146 | B2 | 10/2010 | Kim et al. |
| 7,838,505 | B2 | 11/2010 | Kim et al. |
| 8,435,953 | B2 | 5/2013 | Tabata |
| 8,940,708 | B2 | 1/2015 | Collard et al. |
| 2002/0172663 | A1 | 11/2002 | Palasis |
| 2003/0060403 | A1 | 3/2003 | Nakamura |
| 2003/0148968 | A1 | 8/2003 | Hammond et al. |
| 2003/0171287 | A1 | 9/2003 | Morishita et al. |
| 2003/0176347 | A1 | 9/2003 | Nakamura et al. |
| 2004/0105882 | A1 | 6/2004 | Morishita et al. |
| 2004/0228834 | A1 | 11/2004 | Isner et al. |
| 2005/0079581 | A1 | 4/2005 | Kim et al. |
| 2005/0164208 | A1 | 7/2005 | Poulin |
| 2006/0286072 | A1 | 12/2006 | Giordano et al. |
| 2007/0059288 | A1 | 3/2007 | Dinsmore et al. |
| 2008/0081366 | A1 | 4/2008 | Musunuri et al. |
| 2008/0268030 | A1 | 10/2008 | Morishita et al. |
| 2009/0004260 | A1 | 1/2009 | Morishita et al. |
| 2009/0082293 | A1 | 3/2009 | Giordano et al. |
| 2009/0130761 | A1 | 5/2009 | Koyama et al. |
| 2009/0131350 | A1 | 5/2009 | Kim et al. |
| 2009/0202606 | A1 | 8/2009 | Kim et al. |
| 2009/0258932 | A1 | 10/2009 | Kim et al. |

(Continued)

FOREIGN PATENT DOCUMENTS

| CA | 2 339 378 A1 | 2/2001 |
| CN | 1358543 A | 7/2002 |

(Continued)

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Ishigaki et al, 2007. J Neuropathol Exp Neurol. 66(11): 1037-1044.*
Sun et al, 2002. Journal of Neuroscience. 22(15): 6537-6548.*
Pyun et al (2010. Gene Therapy. 17: 1442-1452).*
Ajroud-Driss et al (2013. Molecular Therapy. 21(6): 1279-1286).*

(Continued)

*Primary Examiner* — John D Ulm
(74) *Attorney, Agent, or Firm* — Fenwick & West LLP

(57) ABSTRACT

The present invention relates to a composition for preventing or treating amyotrophic lateral sclerosis, the composition containing, as an active ingredient, two or more isoforms of a hepatocyte growth factor (HGF) or a polynucleotide encoding the isoforms. The composition of the present invention is used to effectively prevent or treat amyotrophic lateral sclerosis.

11 Claims, 10 Drawing Sheets

Specification includes a Sequence Listing.

(56) References Cited

U.S. PATENT DOCUMENTS

| | | |
|---|---|---|
| 2010/0105878 A1 | 4/2010 | Kim et al. |
| 2011/0166211 A1 | 7/2011 | Kim et al. |
| 2012/0010273 A1 | 1/2012 | Kim et al. |

FOREIGN PATENT DOCUMENTS

| | | |
|---|---|---|
| EP | 0255320 A2 | 7/1987 |
| EP | 0838221 A1 | 4/1998 |
| EP | 1061955 B1 | 5/2005 |
| EP | 1555033 A2 | 7/2005 |
| JP | H11-246433 A | 9/1999 |
| JP | 2006-515855 A | 6/2006 |
| KR | 10-2005-0012208 A | 1/2005 |
| KR | 10-2010-0126316 A | 12/2010 |
| RU | 2413524 C1 | 3/2011 |
| WO | WO 89/01036 A1 | 2/1989 |
| WO | WO 98/50079 A2 | 11/1998 |
| WO | WO 99/36103 A1 | 7/1999 |
| WO | WO 99/45775 A1 | 9/1999 |
| WO | WO 00/40737 A1 | 7/2000 |
| WO | WO 01/34208 A1 | 5/2001 |
| WO | WO 02/22162 A1 | 3/2002 |
| WO | WO 02/089856 A1 | 11/2002 |
| WO | WO 03/078568 A2 | 9/2003 |
| WO | WO 2004/060059 A2 | 7/2004 |
| WO | WO 2007/038056 A2 | 4/2007 |
| WO | WO 2007/058776 A2 | 5/2007 |
| WO | WO 2007/132873 A1 | 11/2007 |
| WO | WO 2007/142651 A1 | 12/2007 |
| WO | WO 2008/121719 A1 | 10/2008 |
| WO | WO 2009/093880 A2 | 7/2009 |
| WO | WO 2012/025925 A1 | 3/2012 |
| WO | WO 2013/037520 A1 | 3/2013 |
| WO | WO 2013/037521 A1 | 3/2013 |

OTHER PUBLICATIONS

Sufit et al, 2015. Amyotrophic Lateral Sclerosis and Frontotemporal Degeneration, vol. 16, Suppl 1:246-247. Abstract No. P303; 2 pages as printed.*

DiBernardo et al., Translating preclinical insights into effective human trials in ALS, 2006, Biochimica et Biophysica Acta 1762:1139-1149.*

Benatar, M., Lost in translation: Treatment trials in the SOD1 mouse and in human ALS, 2007, Neurobiology of Disease 26:1-13.*

Henriques et al., "Neurotrophic growth factors for the treatment of amyotrophic lateral sclerosis: where do we stand?" Front Neurosci. 4:32 (2010) (14 pages).

International Search Report for International Application No. PCT/KR2014/009971, dated Feb. 4, 2015 (7 pages).

Kadoyama et al., "Hepatocyte growth factor (HGF) attenuates gliosis and motoneuronal degeneration in the brainstem motor nuclei of a transgenic mouse model of ALS," Neurosci Res. 59(4):446-56 (2007).

Warita et al., "[Clinical translation of hepatocyte growth factor for amyotrophic lateral sclerosis]," Risho Shinkeigaku. 52(11):1214-7 (2012). (5 pages).

Written Opinion for International Application No. PCT/KR2014/009971, dated Feb. 4, 2015 (9 pages).

Sufit, R.L. et al., "Open Label Study to Assess the Safety of VM202 in Subjects with Amyotrophic Lateral Sclerosis," Amyotrophic Lateral Sclerosis and Frontotemporal Degeneration, 2017, 11 pages, May be Retrieved at URL<http://dx.doi.org/10.1080/21678421.2016.1259334>.

Mitsumoto H, Chad DA, Pioro EP, Amyotrophic Lateral Sclerosis, USA: Oxford University Press, Chapters 15 and 16, 1998, pp. 248-284.

Cozzolino M, Ferri A, Valle C, Carri MT. "Mitochondria and ALS: Implications from Novel Genes and Pathways," Mol Cell Neurosci., 2013, pp. 44-49, vol. 55.

McCombe PA, Henderson RD., "The Role of Immune and Inflammatory Mechanisms in ALS," Curr Mol Med., 2011, pp. 246-254, vol. 11.

Papadimitriou D, Le Verche V, Jacquier A, Ikiz B, Przedborski S, Re DB., "Inflammation in ALS and SMA: Sorting Out the Good from the Evil," Neurobiol Dis., 2010, pp. 493-502, vol. 37.

Barber SC, Shaw PJ., "Oxidative Stress in ALS: Key Role in Motor Neuron Injury and Therapeutic Target," Free Radic Biol Med., 2010, pp. 629-641, vol. 48.

Wallis N, Zagami CJ, Beart PM, O'Shea RD., "Combined Excitotoxic-Oxidative Stress and the Concept of Non-Cell Autonomous Pathology of ALS: Insights into Motoneuron Axonopathy and Astrogliosis," Neurochern Int., 2012, pp. 523-530, vol. 61.

Deloach A, Cozart M, Kiaei A, Kiaei M., "A Retrospective Review of the Progress in Amyotrophic Lateral Sclerosis Drug Discovery Over the Last Decade and a Look at the Latest Strategies," Expert Opin Drug Discov, 2015, pp. 1099-1118, vol. 10.

Miller RG, Mitchell JD, Moore DH., "Riluzole for Amyotrophic Lateral Sclerosis/Motor Neuron Disease," Cochrane Database Syst Rev, 2012, pp. CD001447, vol. 3.

Thomsen G, Gowing G, Sevensen S, Sevenden C., "The Past, Present and Future of Stem Cell Clinical Trials for ALS," Exp Neurol, 2014, pp. 127-137, vol. 262.

Funakoshi H, Nakamura T., "Hepatocyte Growth Factor (HGF): Neurotrophic Functions and Therapeutic Implications or Neuronal Injury/Diseases," Curr Signal Transduct Ther, 2011, pp. 156-167, vol. 6.

Sun W, Funakoshi H, Nakamura T., "Overexpression of HGF Retards Disease Progression and Prolongs Life Span in a Transgenic Mouse Model of ALS," J Neurosci., 2002, pp. 6537-6548 vol. 22.

Ishigaki A, Aoki M, Nagai M, Warita H, Kato S, Kato M, et al., "Intrathecal Delivery of Hepatocyte Growth Factor from Amyotrophic Lateral Sclerosis Onset Suppresses Disease Progression in Rat Amyotrophic Lateral Sclerosis Model," J Neuropathol Exp Neurol., 2007, pp. 1037-1044, vol. 66.

Nakamura T, Sakai K, Nakamura T, Matsumoto K., "Hepatocyte Growth Factor Twenty Years on: Much More Than a Growth Factor," J Gastroenterol Hepatol, 2011, pp. 188-202, vol. Suppl 1.

Akita H, Takagi N, Ishihara N, Takagi K, Murotomi K, Funakoshi H, et al., "Hepatocyte Growth Factor Improves Synaptic Localization of the NMDA Receptor and Intracellular Signaling After Excitotoxic Injury in Cultured Hippocampal Neurons," Exp Neurol, 2008, pp. 83-94, vol. 210.

Ishihara N, Takagi N, Niimura M, Takagi K, Nakano M, Tanonaka k, et al., "Inhibition of Apoptosis-Inducing Factor Translocation is linvolved in Protective Effects of Hepatocyte Growth Factor Against Excitotoxic Cell Death in Cultured Hippocampal Neurons," J Neurochem, 2005, pp. 1277-1286, vol. 95.

Pasinelli P, Houseweart MK, Brown RH, Jr, Cleveland DW, "Caspase-1 and -3 are Sequentially Activated in Motor Neuron Death in Cu, Zn Superoxide Dismutase-Mediated Familial Amyotrophic Lateral Sclerosis," Proc Natl Acad Sci USA, 2000, pp. 13901-13906, vol. 97.

Kadoyama K, Funakoshi H, Ohya W, Nakamura T, "Hepatocyte Growth Factor (HGF) Attenuates Gliosis and Motoneuronal Degeneration in the Brainstem Motor Nuclei of a Transgenic Mouse Model of ALS," Neurosci Res, 2007, pp. 446-456, vol. 59.

Tyndall SJ, Walikonis RS, "Signaling by Hepatocyte Growth Factor in Neurons is Induced by Pharmacological Stimulation of Synaptic Activity," Synapse, 2007, pp. 199-204, vol. 61.

Shang J, Deguchi K, Ohta Y, Liu N, Zhang X, Tian F, et al., "Strong Neurogenesis, Angiogenesis, Synaptogenesis, and Antifibrosis of Hepatocyte Growth Factor in Rats Brain after Transient Middle Cerebral Artery Occlusion," J Neurosci Res, 2011, pp. 86-95, vol. 89.

Yuan J, Yankner BA., "Apoptosis in the Nervous System," Nature, 2000, pp. 802-809, vol. 407.

Martin LJ. Neuronal Death in Amyotrophic Lateral Sclerosis is Aapoptosis: Possible Contribution of a Programmed Cell Death Mechanism. J Neuropathol Exp Neurol. 1999, pp. 459-471, vol. 58.

Kadoyama K, Funakoshi H, Ohya-Shimada W, Nakamura T, Matsumoto K, Matsuyama S, et al. Disease-dependent Reciprocal Phosphorylation of Serine and Tyrosine Residues of c-Met/HGF Receptor Contributes Disease Retardation of a Transgenic Mouse Model of ALS. Neurosci Res. 2009, pp. 194-200, vol. 65.

(56) References Cited

OTHER PUBLICATIONS

Pyun WB, Hahn W, Kim DS, Yoo WS, Lee SD, Won JH, et al. Naked DNA Expressing Two Isoforms of Hepatocyte Growth Factor induces Collateral Artery Augmentation in a Rabbit Model of Limb Ischemia. Gene Ther. 2010, pp. 1442-152, vol. 17.
Hahn W, Pyun WB, Kim DS, Yoo WS, Lee SD, Won JH, et al. Enhanced Cardioprotective Effects by Coexpression of Two Isoforms of Hepatocyte Growth Factor from Naked Plasmid DNA in a Rat Ischemic Heart Disease Model. J Gene Med. 2011, pp. 549-555, vol. 13.
Ajroud-Driss S, Christiansen M, Allen JA, Kessler JA. Phase 1/2 Open-Label Dose-Escalation Study of Plasmid DNA Expressing Two Isoforms of Hepatocyte Growth Factor in Patients with Painful Diabetic Peripheral Neuropathy. Mol Ther. 2013, pp. 1279-1286, vol. 21.
Henry TD, Hirsch AT, Goldman J, Wang YL, Lips DL, McMillan WD, et al. Safety of a Non-Viral Plasmid-Encoding Dual Isoforms of Hepatocyte Growth Factor in Critical Limb Ischemia Patients: a Phase I Study. Gene Ther. 2011, pp. 788-794, vol. 18.
Kessler JA, Smith AG, Cha BS, Choi SH, Wymer H, Shaibani A, et al., "Double-Blind, Placebo-Controlled Study of HGF Gene Therapy in Diabetic Neuropathy." Ann Clin Transl Neurol, 2015, pp. 465-478, vol. 2.
Kim JS, Hwang HY, Cho KR, Park EA, Lee W, Paeng JC, et al., "Intramyocardial Transfer of Hepatocyte Growth Factor as an Adjunct to CABG: Phase I Clinical Study," Gene Ther, 2013, pp. 717-722, vol. 20.
Kibbe MR, Hirsch AT,Medelsohn FO, Daies MG, Pham H, Saucedo J, et al., "Safety and Efficacy of Plasmid DNA Expressing Two Isoform of Hepatocyte Growth Factor in Patients with Critical Limb Ischemia," Gene Ther, 2016, pp. 306-312, vol. 23.
Gordon PH, Moore DH, Miller RG, Florence JM, Verheijde JL, Doorish C, et al., "Efficacy of Minocycline in Patients with Amyotrophic Lateral Sclerosis: a Phase III Randomised Trial," Lancet Neurol, 2007, pp. 1045-1053, vol. 6.
Seki, T., et al., "Organization of the Human Hepatocyte Growth Factor-Encoding Gene," Gene, Elsevier Science Publishers B.V., 1991, pp. 213-219, vol. 102.
Supplementary European Search Report for European Application No. EP 03 74 4561, European Patent Office, Netherlands, dated Apr. 18, 2006.
Seki, T., et al., "Isolation and Expression of cDNA for Different Forms of Hepatocyte Growth Factor from Human Leukocyte," Biochem. Biophys. Res. Commun., , Academic Press, 1990, pp. 321-327, vol. 172.
Shima, N., et al., "Hepatocyte Growth Factor and its Variant with a Deletion of Five Amino Acids are Distinguishable in their Biological Activity and Tertiary Structure," Biochem. Biophys. Res. Commun., Academic Press, 1994, pp. 808-815, vol. 200, No. 2.
NCBI Entrez, GenBank Database, Accession No. AC004960, "*Homo sapiens* PAC clone RP5-1098B1 from 7q11.23-q21, complete sequence," 41 pages (first available 1998).
Deng, et al., "Secretory Expression of the Deleted Variant of Human Hepatocyte Growth Factor (hdHGF) in Pichia pastoris," Chinese Journal of Biochemistry and Molecular Biology 17:590-594 (2001), China Academic Journal Electronic Publishing House, Beijing, China. [With English abstract].
Romano, G. et al., "Gene Transfer Technology in Therapy: Current Applications and Future Goals," Stem Cells, 1999, pp. 191-202, vol. 17.
Liu, F. et al., "Development of Non-Viral Vectors for Systemic Gene Delivery," Journal of Controlled Release, Jan. 17, 2002, pp. 259-266, vol. 78, Issues 1-3.
Schmitz, V. et al., "Gene Therapy for Liver Diseases: Recent Strategies for Treatment of Viral Hepatitis and Liver Malignancies," Gut. Jan. 2002, pp. 130-135, vol. 50, No. 1.
Office Action for Co-Pending U.S. Appl. No. 10/944,277, dated Feb. 13, 2009.
Notice of Allowance and Fees Due for Co-Pending U.S. Appl. No. 10/944,277, dated May 29, 2009.
Notice of Allowance and Fees Due for Co-Pending U.S. Appl. No. 10/944,277, dated Oct. 23, 2009.
Co-Pending U.S. Appl. No. 12/650,860, inventors Kim et al., filed Dec. 31, 2009 (Not Yet Published). [Copy Not Enclosed].
Notice of Allowance and Fees Due for Co-Pending U.S. Appl. No. 12/650,860, dated Mar. 10, 2010.
Esp@cenet Database, English language abstract of JP 11-246433 A, published Sep. 14, 1999.
Kato, N. et al., "Nonviral HVJ (Hemagglutinating Virus of Japan) Liposome-Mediated Retrograde Gene Transfer of Human Hepatocyte Growth Factor into Rat Nervous System Promotes Functional and Histological Recovery of the Crushed Nerve," Neuroscience Research, Elsevier Ireland Ltd and the Japan Neuroscience Society 2005, pp. 299-310, vol. 52.
Yang, J. et al., "Sustained Expression of Naked Plasmid DNA Encoding Hepatocyte Growth Factor in Mice Promotes Liver and Overall Body Growth," Hepatology American Assoc. for the Study of Liver Disease, 2001, pp. 848-859, vol. 33, No. 4.
Office Action for U.S. Appl. No. 10/944,277 (now U.S. Pat. No. 7,812,146), dated Jan. 9, 2008.
Office Action for U.S. Appl. No. 11/957,170 (now U.S. Pat. No. 7,838,505), dated Jan. 28, 2010.
Notice of Allowance for U.S. Appl. No. 11/957,170 (now U.S. Pat. No. 7,838,505), dated Jul. 19, 2010.
Office Action for Co-pending U.S. Appl. No. 12/359,137, dated Apr. 28, 2011.
Office Action for Co-pending U.S. Appl. No. 12/421,425, dated Aug. 19, 2010.
Office Action for Co-pending U.S. Appl. No. 12/421,425, dated Dec. 17, 2010.
U.S. Appl. No. 13/045,460, filed Mar. 10, 2011 (not yet published). [Copy Not Enclosed].
Brus, C. et al., "Stabilization of Oligonucleotide-Polyethylenimine Complexes by Freeze-Drying: Physiochemical and Biological Characterization," Journal of Controlled Release, 2004; pp. 119-131, vol. 95.
Taniyama, Y. et al., "Therapeutic Antiogenesis Induced by Human Hepatocyte Growth Factor Gene in Rat and Rabbit Hindlimb Ischemia Models: Preclinical Study for Treatment of Peripheral Arterial Disease," Gene Therapy, 2001, pp. 181-189, vol. 8.
Morishita, R. et al., "Therapeutic Angiogenesis using Hepatocyte Growth Factor (HGF)" Current Gene Therapy, Bentham Science Publishers Ltd., 2004, pp. 199-206, vol. 4.
Nakagami, H. et al., "Hepatocyte Growth Factor as Potential Cardiovascular Therapy" Expert Review of Cardiovascular Therapy, Future Drugs Ltd., 2005, pp. 513-519, vol. 3, No. 3.
Liu. Y., et al., "Secretory Expression and Characterization of a Recombinant-Deleted Variant of Human Hepatocyte Growth Factor in Pichia pastoris," World Journal of Gastroenterology, World Journal of Gastroenterology, China, 2005, pp. 7097-7103, vol. vol. 11, No. 45.
Romano, G., "Gene Transfer in Experimental Medicine," Drug News Perspect, 2003, pp. 267-276, vol. 16, No. 5.
Kaiser, J., "Death Prompts a Review of Gene Therapy Vector," Science, Aug. 3, 2007, p. 580, vol. 317.
De Palma, M. et al., "In Vivo Targeting of Tumor Endothelial Cells by Systemic Delivery of Lentiviral Vectors," Human Gene Therapy, Aug. 10, 2003, pp. 1193-1206, vol. 14, No. 12.
Soofiyani, S.R. et al., "Gene Therapy, Early Promises, Subsequent Problems, and Recent Breakthroughs," Advanced Pharmaceutical Bulletin, 2013, pp. 249-255, vol. 3, No. 2.
Eck, S.L. et al., "Chapter 5: Gene-Based Therapy," Goodman & Gilman's The Pharmacological basis of Therapeutics, 1996, McGraw-Hill, New York, NY. pp. 77-101.
Gautam, A. et al., "Delivery Systems for Pulmonary Gene Therapy," Am. J. Respir. Med., 2002, pp. 35-46, vol. 1, Issue 1.
Kay, M.A., "State-of-the-Art Gene-Based Therapies: The Road Ahead," Nature Reviews Genetics, May 2011, pp. 316-328, vol. 12.
International Search Report for International Application No. PCT/KR2012/002224, dated Oct. 12, 2012.
Kim, J-M. et al., "Development of Innovative Biomedicine: A Case Study on Cardiovascular Gene Medicine Using Naked DNA Express-

(56) References Cited

OTHER PUBLICATIONS ing Two Isoforms of Hepatooyte Growth Factor," Second Workshop of New Medicine Developer, ViroMed Co. Ltd., published Jun. 1, 2011 (55 pages).
Tolbert, W.D. et al., "Structural Basis for Agonism and Antagonism of Hepatocyte Growth Factor," PNAS, Jul. 27, 2010, pp. 13264-13269, vol. 107, No. 30.
Aoki, M., et al., "Angiogenesis Induced by Hepatocyte Growth Factor in Non-Infarcted Myocardium and Infarcted Myocardium: Up-Regulation of Essential Transcription Factor for Angiogenesis, ets," Gene Therapy, Macmillian Publishers Ltd, England 2000, pp. 417-427, vol. 7.
Azuma, J. et al., "Angiogenic and Antifibrotic Actions of Hepatocyte Growth Factor Improve Cardiac Dysfunction in Porcine Ischemic Cardiomyopathy," Gene Therapy, Nature Publishing Group, England, 2006, pp. 1206-1213, vol. 3.
Funatsu, T., et al., "Therapeutic Angiogenesis in the Ischemic Canine Heart Induced by Myocardial Injection of Naked Complementary DNA Plasmid Encoding Hepatocyte Growth Factor," J Thorac. Cardiovasc. Surg., American Association for Thoracic Surgery, United States, 2002, pp. 1099-1105, vol. 124, No. 6.
Cho, K.R., et al., "Therapeutic angiogenesis using naked DNA expressing two isoforms of the hepatocyte growth factor in a porcine acute myocardial infarction model," Eur. J Cardiothorac. Surg., Elsevier B.V., Netherlands, Oct. 2008, pp. 857-863, vol. 34, No. 4.
Hahn, W., et al., "Development of Novel Angiogenic DNA Medicine Using a Genomic/cDNA Hybrid of Hepatocyte Growth Factor Gene," Molecular Therapy Journal, Abstract of Article 876, The American Society of Gene Therapy, United States, 2006, p. S337, vol. 13, Suppl. 1.
Jayasankar, V. et al., "Gene Transfer of Hepatocyte Growth Factor Attenuates Postinfarction Heart Failure," Circulation, American Heart Association, Inc., United States, 2003, pp. Il-230-IL236, vol. 108(90/01).
Saeed, M., et al., "MR Assessment of Myocardial Perfusion, Viability, and Function after Intramyocardial Transfer of VM202, a New Plasmid Human Hepatocyte Growth Factor in Ischemic Swine Myocardium," Radiology 249(1): 107-118, RSNA Radiological Society of North America, United States (Oct. 2008).
Wang, W., et al., "Induction of Collateral Artery Growth and Improvement of Post-Infarct Heart Function by Hepatocyte Growth Factor Gene Transfer," Acta. Pharmacol. Sin., Blackwell Publishing, England, 2006, pp. 555-560, vol. 27, No. 5.
Supplementary European Search Report with Written Opinion for European Application No. EP 09 70 4660, European Patent Office, Germany, dated Aug. 7, 2012.
Yamaguchi, T. et al., "Therapeutic Angiogenesis Induced by Injecting Hepatocyte Growth Factor in Ischemic Canine Hearts," Surgery Today, First Department of Surgery, Osaka University Medical School, Springer-Verlag, 2005, pp. 855-860, vol. 35, No. 10.
Office Action for U.S. Appl. No. 13/045,460, dated Nov. 16, 2011.
Office Action for U.S. Appl. No. 13/045,460, dated Feb. 16, 2012.
Perin et al. (2011) Human hepatocyte growth factor (VM202) gene therapy via transendocardial injection in a pig model of chronic myocardial ischemia. Journal of Cardiac Failure 17(7): 601-611.
Montesano, R., et al., "Differential Effects of Hepatocyte Growth Factor Isoforms on Epithelial and Endothelial Tubulogenesis." Cell Growth & Differentiation, Geneva, Switzerland, May 1998, pp. 355-365, vol. 9.
Co-pending Application, U.S. Appl. No. 12/908,765, inventors Kim, et al., filed Oct. 20, 2010 (Not Published) [Copy Not Enclosed].
International Search Report and Written Opinion, PCT Application No. PCT/KR2015/010240, dated Jan. 20, 2016.
Atassi, N. et al., "The PRO-ACT Database: Design, Initial Analyses, and Predictive Features," The American Academy of Neurology, 2014, pp. 1719-1725.
Bansal, V. et al., "Diabetic Neuropathy," Postgrad Med. J., Jun. 16, 2006, pp. 95-100, vol. 82.
Brinkmann, J.R. et al., "Guidelines for the Use and Performance of Quantitative Outcome Measures in ALS Clinical Trials," Journal of Neurological Sciences, 1997, pp. 97-111, vol. 147.
Carlsson, M. et al., "Quantitative MR Measurements of Regional and Global Left Ventricular Function and Strain After Intramyocardial Transfer of VM202 Into Infarcted Swine Myocardium," Am. J. Physiol. Heart Circ. Physiol., 2008, pp. H522-H532, vol. 295.
Cedarbaum, J.M. et al., "The ALSFRS-R: A Revised ALS Functional Rating Scale That Incorporates Assessments of Respiratory Function," Journal of the Neurological Sciences, 1999, pp. 13-21, vol. 169.
Cruzado, J.M. et al., "Regression of Advanced Diabetic Nephropathy by Hepacyte Growth Factor Gene Therapy in Rats," Diabetes, Apr. 2004, pp. 1119-1127, vol. 53.
Körner, S. et al., "Interaction of Physical Function, Quality of Life and Depression in Amyotrophic Lateral Sclerosis: Characterization of a Large Patient Cohort," BMC Neurology, 2015, 8 pages, vol. 15, No. 84.
NCBI Reference Sequence: NP_000592.3, "Hepatocyte growth factor isoform 1 preproprotein [*Homo sapiens*]," GenBank Database, Accession NP_000592.3, 3 pages, Sep. 29, 2013.
Saeed, M. et al., "Cardiovascular Magnetic Resonance Imaging in Delivering and Evaluating the Efficacy of Hepatocyte Growth Factor Gene in Chronic Infarct Scar," Cardiovasc Revasc Med., 2011, pp. 111-122, vol. 12, No. 2.
Simovic, D. et al., "Improvement in Chronic Ischemic Neuropathy After Intramuscular phVEGF165 Gene Transfer in Patients with Critical Limb Ischemia Free," Arch. Neurol., 2001, pp. 761-768, vol. 58, No. 5.
Canadian Office Action, Canadian Application No. 2,926,607, dated Feb. 20, 2017, 3 pages.
European Supplementary Search Report, European Application No. 14856385, dated Apr. 25, 2017, 7 pages.
Gu, Y. et al., "A Phase I Clinical Study of Naked DNA Expressing Two Isoforms of Hepatocyte Growth Factor to Treat Patients with Critical Limb Ischemia," The Journal of Gene Medicine, 2011, pp. 602-610, vol. 13.
Japanese Office Action, Japanese Application No. 2016-546724, dated Jun. 6, 2017, 12 pages (with concise explanation of relevance).
Korean Office Action, Korean Application No. 10-2014-0143377, dated Apr. 19, 2017, 17 pages (with concise explanation of relevance).
Korean Office Action, Korean Application No. 10-2014-0143377, dated Jan. 19, 2017, 19 pages (with concise explanation of relevance).
Korean Office Action, Korean Application No. 10-2014-0143377, dated Oct. 27, 2016, 25 pages (with concise explanation of relevance).
Korean Office Action, Korean Application No. 10-2014-0143377, dated Apr. 20, 2016, 6 pages (with concise explanation of relevance).
Nakamura, T. et al., Hepatocyte Growth Factor Twenty Years on: Much More Than a Growth Factor, Journal of Gastroenterology and Hepatology, 2011, pp. 188-202, vol. 26, Suppl. 1.
Russian Office Action, Russian Application No. 2016119116/15 (030011), dated Jul. 4, 2017, 11 pages.
Singapore Search Report and Written Opinion, Singapore Application No. 11201602452S, dated Mar. 27, 2017, 9 pages.
BioBox All Secrets, Sep. 29, 2012, 8 pages, [Online] [Retrieved on Aug. 8, 2017] Retrieved from the Internet<URL:http://biobox.spb.ru/lektsii/biokhimiya/135-belki.html> [with concise explanation of relevance].
Database GenBank, BAF94363.1, Jan. 9, 2008, NCBI, 3 pages, [Online] [Retrieved on Aug. 8, 2017] Retrieved from the Internet<URL:https://www.ncbi.nlm.nih.gov/protein/158256780?report=genbank&log$=prottop&blast_rank=6&RID=NMF0W1WY014.
Aoki, M., "Hepatocyte Growth Factor Therapy for Amyotrophic Lateral Sclerosis," Brain Nerve, Mar. 2012, pp. 245-254, vol. 64, No. 3, [with English abstract].

(56) References Cited

OTHER PUBLICATIONS

Esaki, S. et al., "Hepatocyte Growth Factor Incorporated Into Herpes Simplex Virus Vector Accelerates Facial Nerve Regeneration After Crush Injury," Gene Therapy, 2011, pp. 1063-1069, vol. 18.

Funakoshi, H. et al., "ALS and Neurotrophic Factors—HGF as a Novel Neurotrophic and Neuroregenerative Factor," Brain Nerve, Oct. 2007, pp. 1195-1202, vol. 59, No. 10, [with English abstract].

Ishigaki, A. et al., "Intrathecal Delivery of Hepatocyte Growth Factor From Amyotrophic Lateral Sclerosis Onset Suppresses Disease Progression in Rat Amyotrophic Lateral Sclerosis Model," Journal of Neuropathology & Experimental Neurology, Nov. 2007, pp. 1037-1044, vol. 66, No. 11.

Kato, N. et al., "Nonviral HVJ (Hemagglutinating Virus of Japan) Liposome-Mediated Retrograde Gene Transfer of Human Hepatocyte Growth Factor into Rat Nervous System Promotes Functional and Histological Recovery of the Crushed Nerve," Neuroscience Research, 2005, pp. 299-310, vol. 52.

"Kringle Initiates Phase I/II Clinical Trial of Recombinant Human HGF for the Treatment of Acute Spinal Cord Injury," Kringle Pharma, Jun. 16, 2014, 2 pages.

Reyes-Gibby, C.C. et al., "Informative Gene Network for Chemotherapy-Induced Peripheral Neuropathy," BioData Mining, 2015, pp. 1-23, vol. 8, No. 24.

Tsuchihara, T. et al., "Nonviral Retrograde Gene Transfer of Human Hepatocyte Growth Factor Improves Neuropathic Pain-Related Phenomena in Rats," Molecular Therapy, Jan. 2009, pp. 42-50, vol. 17, No. 1.

Wong, V. et al., "Hepatocyte Growth Factor Promotes Motor Neuron Survival and Synergizes with Ciliary Neurotrophic Factor," The Journal of Biological Chemistry, Feb. 21, 1997, pp. 5187-5191, vol. 272, No. 8.

European Extended Search Report, European Application No. 14856385.1, dated May 9, 2017, 8 pages.

Database WPI Week 200239, Thomson Scientific, AN 2002-362306, Clarivate Analytics, 2017, 3 pages.

Database WPI Week 200540, Thomson Scientific, AN 2005-392869, Clarivate Analytics, 2017, 2 pages.

* cited by examiner

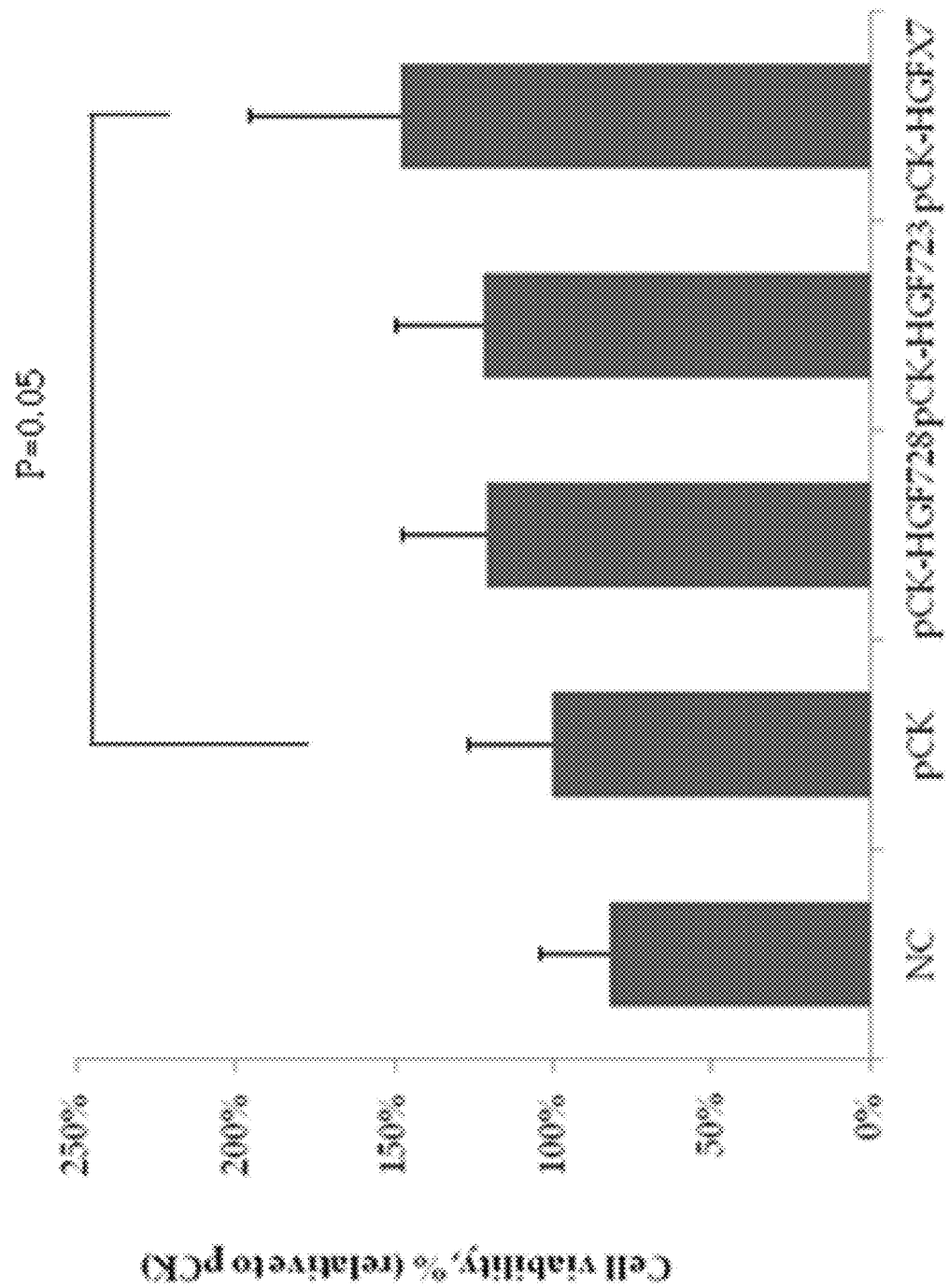

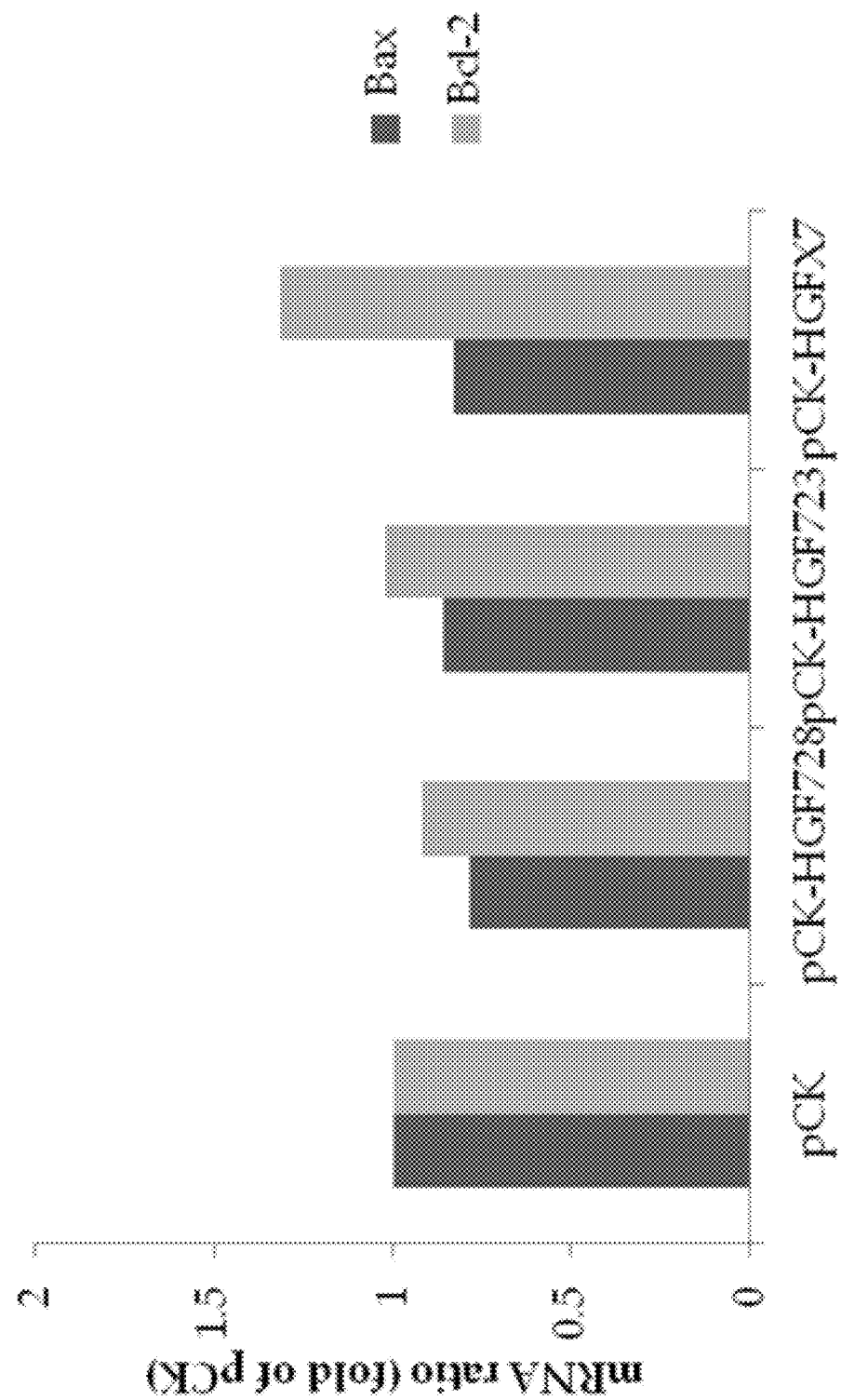

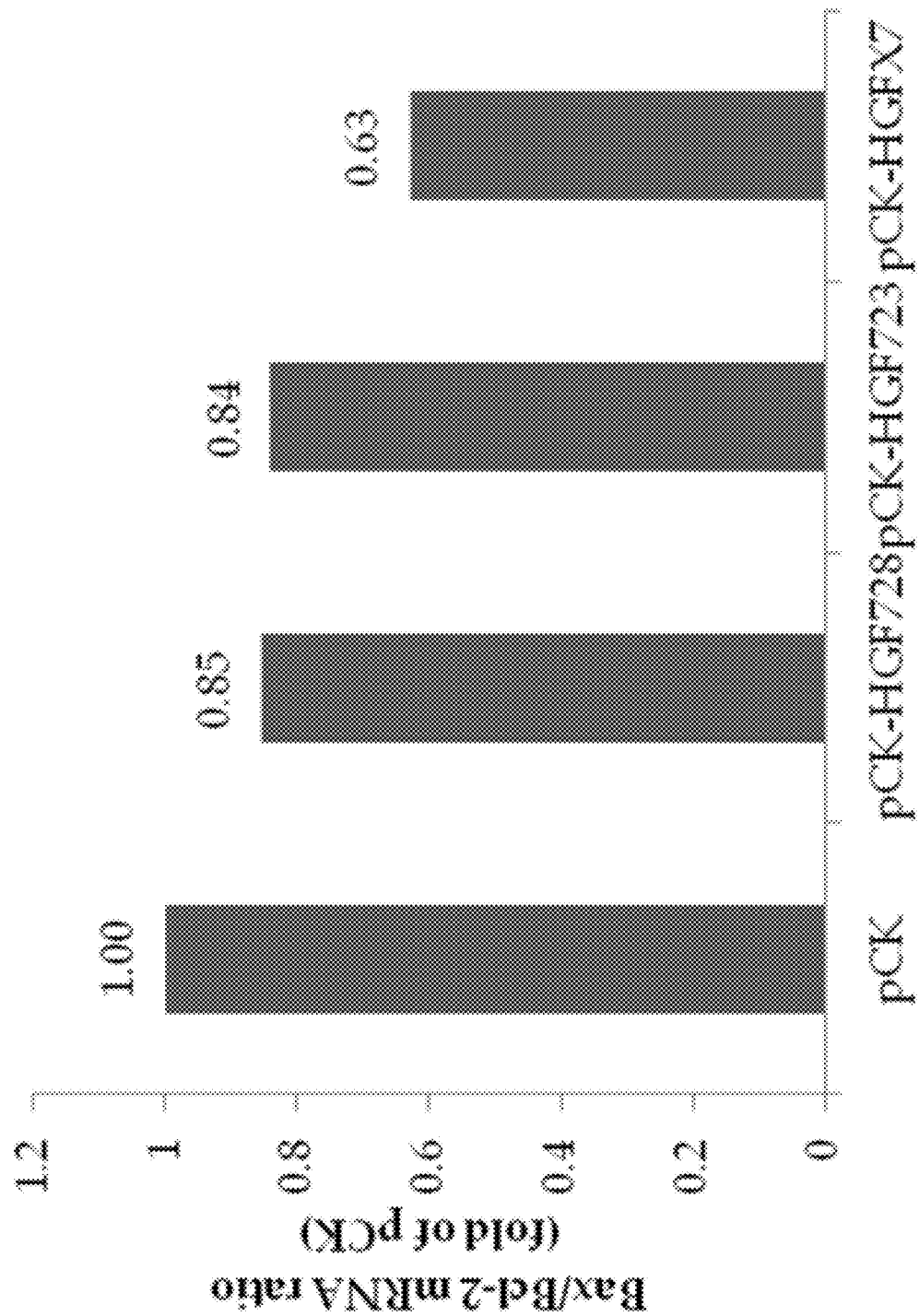

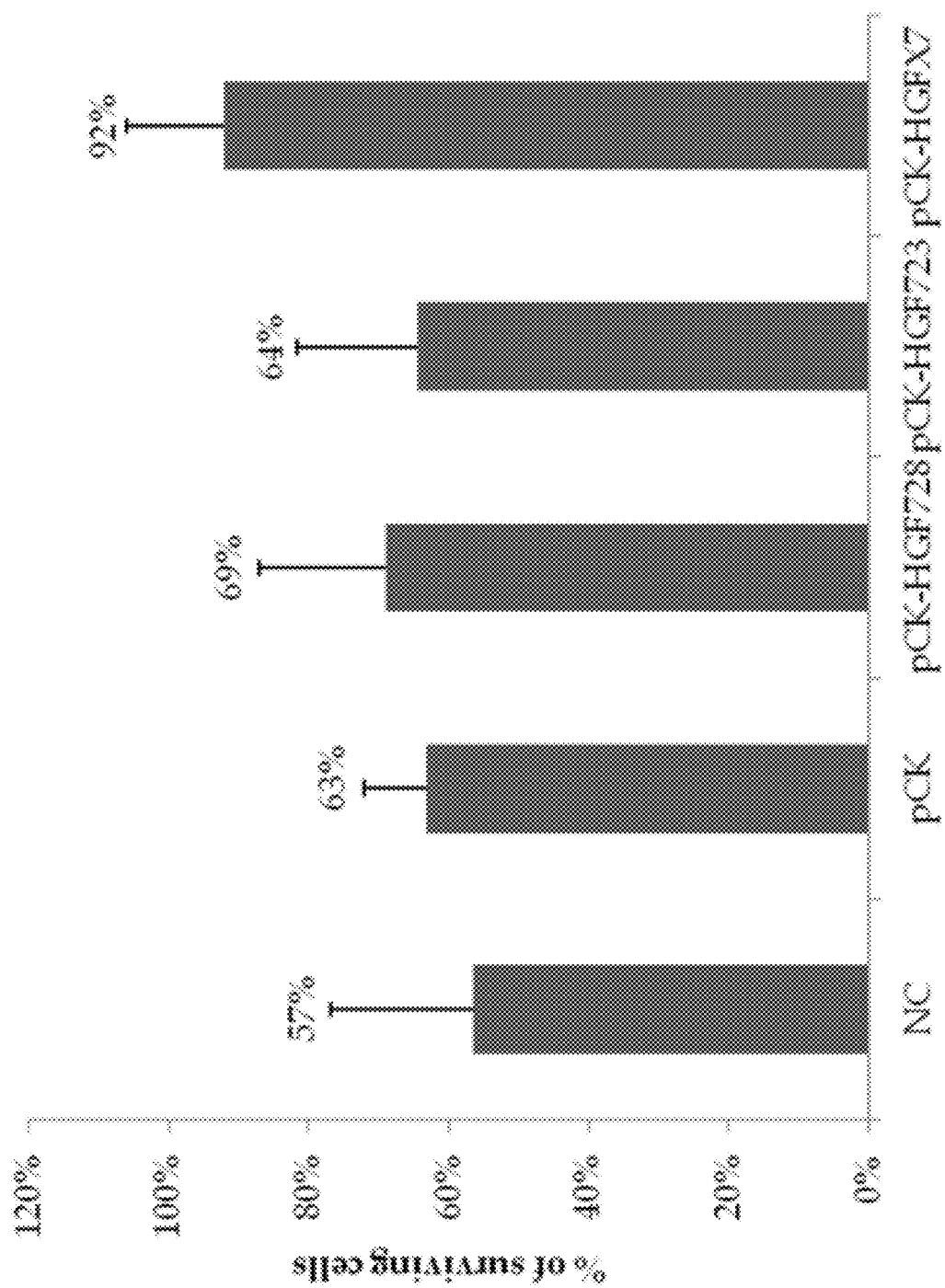

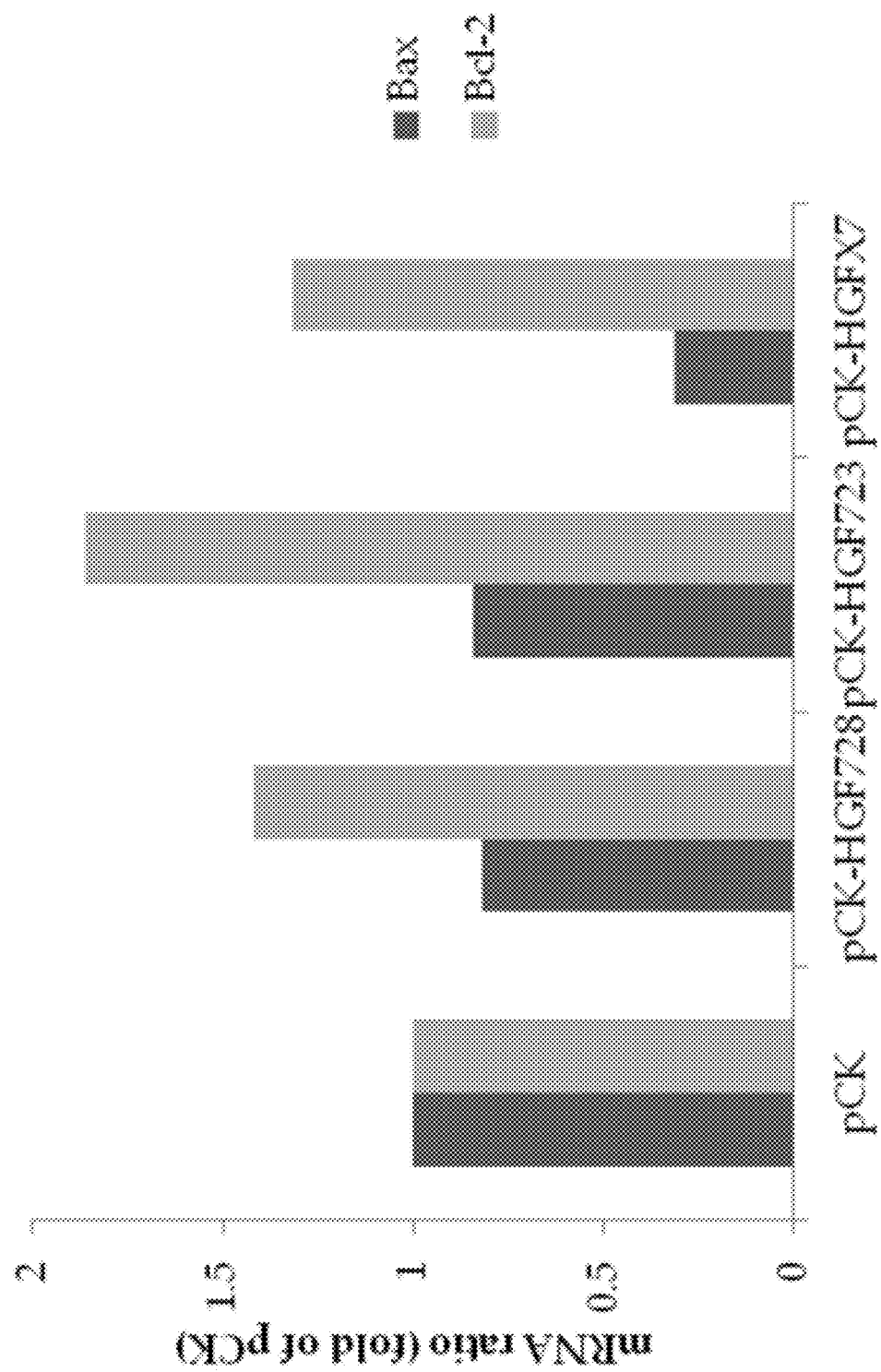

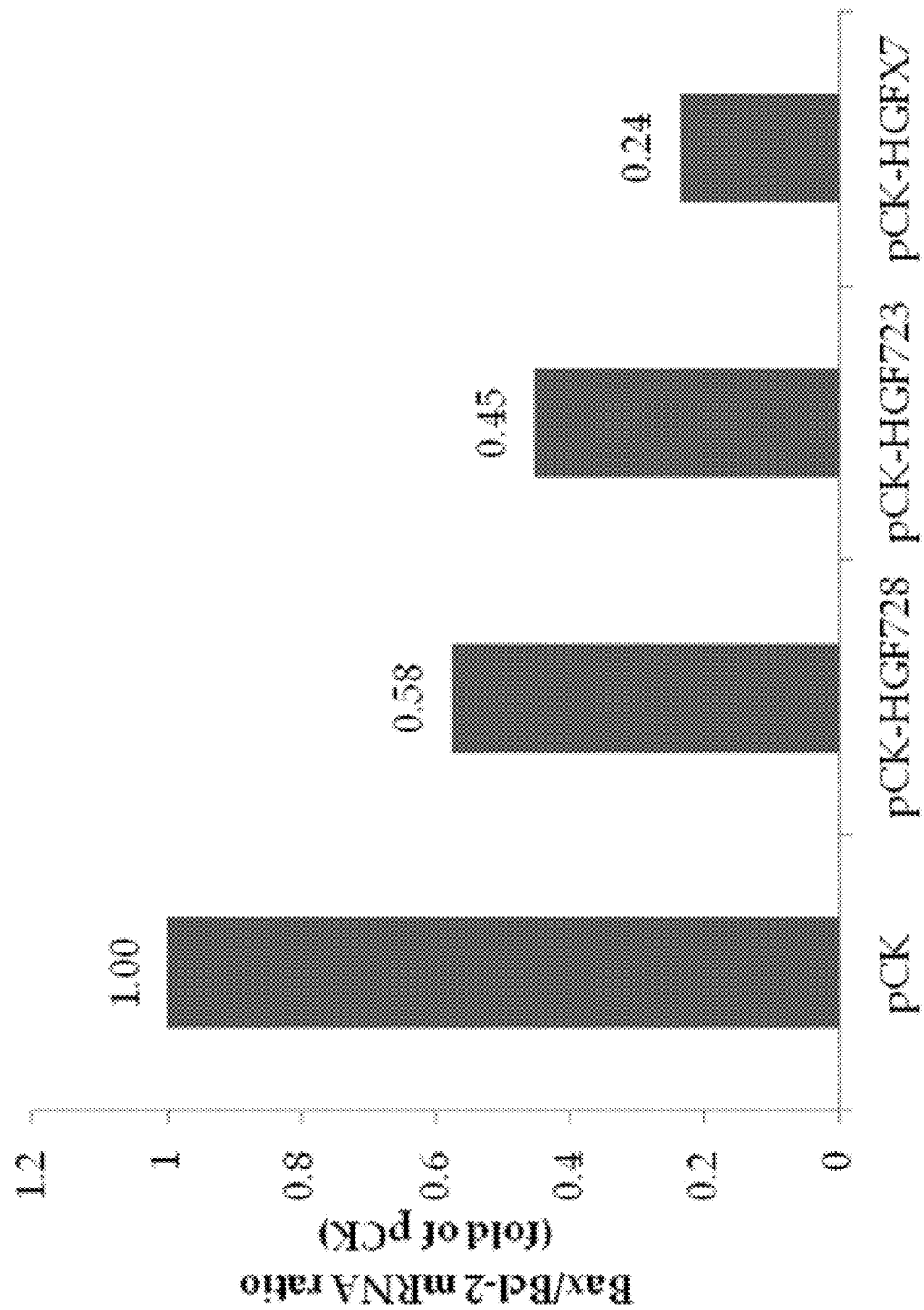

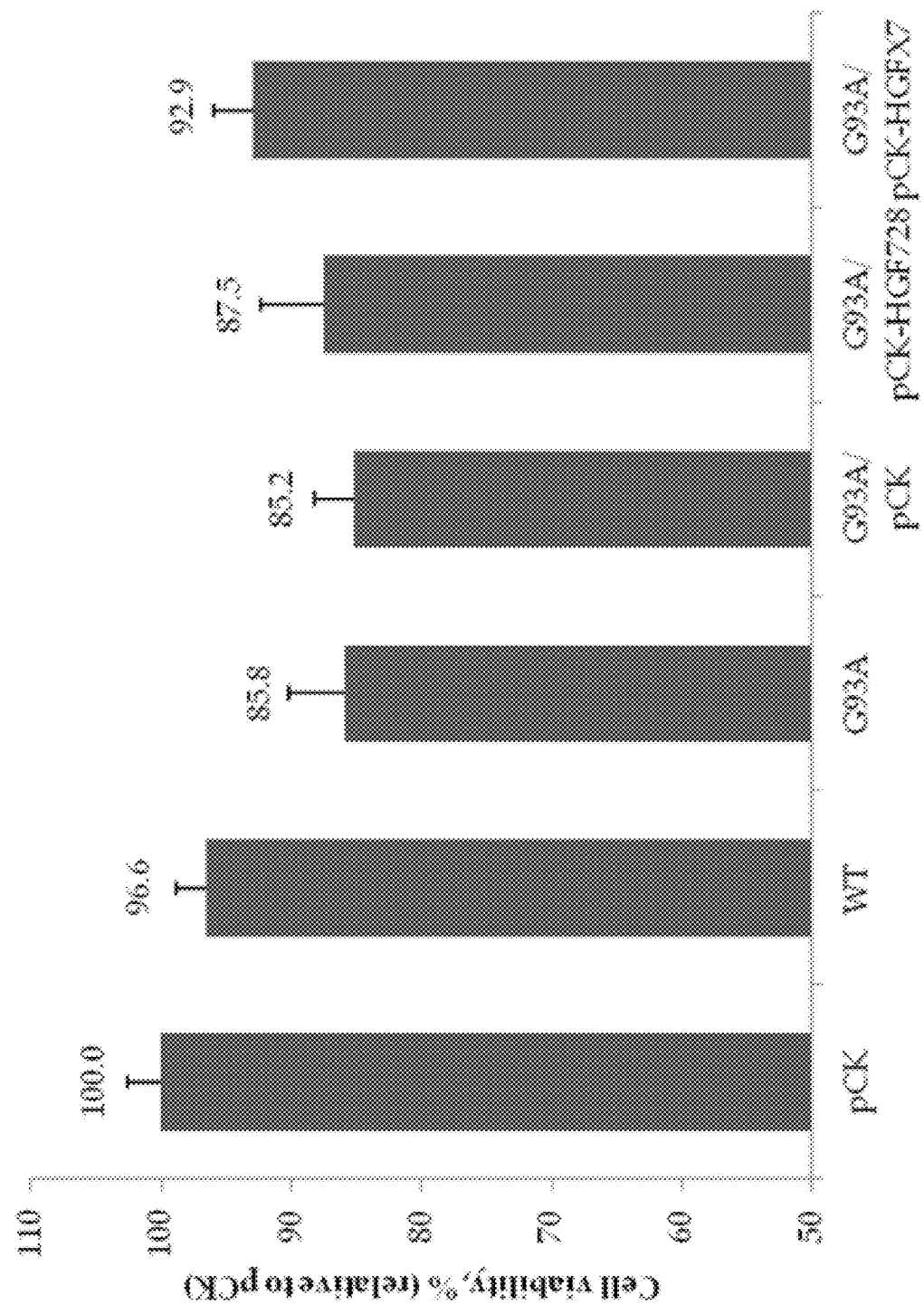

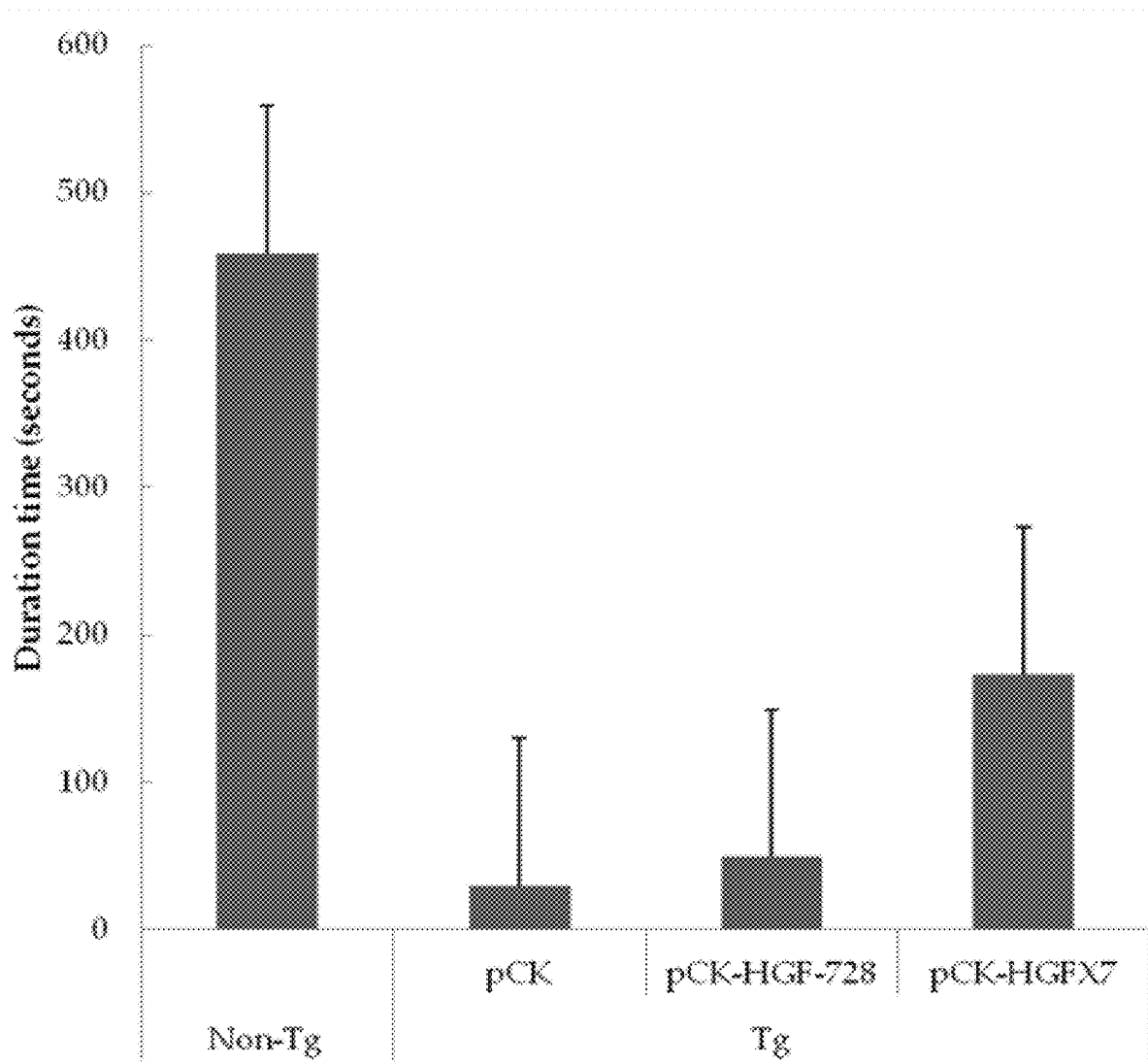

SEQUENCE LISTING

```
<160> NUMBER OF SEQ ID NOS: 16

<210> SEQ ID NO 1
<211> LENGTH: 728
<212> TYPE: PRT
<213> ORGANISM: Artificial Sequence
<220> FEATURE:
<223> OTHER INFORMATION: amino acid sequence of flHGF

<400> SEQUENCE: 1

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30
```

-continued

Arg Lys Arg Arg Asn Thr Ile His Glu Phe Lys Lys Ser Ala Lys Thr
         35                  40                  45

Thr Leu Ile Lys Ile Asp Pro Ala Leu Lys Ile Lys Thr Lys Lys Val
 50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
        210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
        290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

```
Gly Pro Trp Cys Tyr Thr Gly Asn Pro Leu Ile Pro Trp Asp Tyr Cys
    450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
            500                 505                 510
Tyr Arg Asn Lys His Ile Cys Gly Gly Ser Leu Ile Lys Glu Ser Trp
        515                 520                 525
Val Leu Thr Ala Arg Gln Cys Phe Pro Ser Arg Asp Leu Lys Asp Tyr
    530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
            580                 585                 590
Phe Val Ser Thr Ile Asp Leu Pro Asn Tyr Gly Cys Thr Ile Pro Glu
        595                 600                 605
Lys Thr Ser Cys Ser Val Tyr Gly Trp Gly Tyr Thr Gly Leu Ile Asn
    610                 615                 620
Tyr Asp Gly Leu Leu Arg Val Ala His Leu Tyr Ile Met Gly Asn Glu
625                 630                 635                 640
Lys Cys Ser Gln His His Arg Gly Lys Val Thr Leu Asn Glu Ser Glu
                645                 650                 655
Ile Cys Ala Gly Ala Glu Lys Ile Gly Ser Gly Pro Cys Glu Gly Asp
            660                 665                 670
Tyr Gly Gly Pro Leu Val Cys Glu Gln His Lys Met Arg Met Val Leu
        675                 680                 685
Gly Val Ile Val Pro Gly Arg Gly Cys Ala Ile Pro Asn Arg Pro Gly
    690                 695                 700
Ile Phe Val Arg Val Ala Tyr Tyr Ala Lys Trp Ile His Lys Ile Ile
705                 710                 715                 720
Leu Thr Tyr Lys Val Pro Gln Ser
                725

<210> SEQ ID NO 2
<211> LENGTH: 723
<212> TYPE: PRT
<213> ORGANISM: Artificial Sequence
<220> FEATURE:
<223> OTHER INFORMATION: amino acid sequence of dHGF

<400> SEQUENCE: 2

Met Trp Val Thr Lys Leu Leu Pro Ala Leu Leu Leu Gln His Val Leu
1               5                   10                  15
Leu His Leu Leu Leu Leu Pro Ile Ala Ile Pro Tyr Ala Glu Gly Gln
                20                  25                  30
Arg Lys Arg Arg Asn Thr Ile His Glu Phe Lys Lys Ser Ala Lys Thr
            35                  40                  45
Thr Leu Ile Lys Ile Asp Pro Ala Leu Lys Ile Lys Thr Lys Lys Val
        50                  55                  60
Asn Thr Ala Asp Gln Cys Ala Asn Arg Cys Thr Arg Asn Lys Gly Leu
65                  70                  75                  80
```

-continued

```
Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
        275                 280                 285

Asn Asp Thr Asp Val Pro Leu Glu Thr Thr Glu Cys Ile Gln Gly Gln
290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
            340                 345                 350

Asp Gly Ser Glu Ser Pro Trp Cys Phe Thr Thr Asp Pro Asn Ile Arg
        355                 360                 365

Val Gly Tyr Cys Ser Gln Ile Pro Asn Cys Asp Met Ser His Gly Gln
370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415

Leu His Arg His Ile Phe Trp Glu Pro Asp Ala Ser Lys Leu Asn Glu
            420                 425                 430

Asn Tyr Cys Arg Asn Pro Asp Asp Asp Ala His Gly Pro Trp Cys Tyr
        435                 440                 445

Thr Gly Asn Pro Leu Ile Pro Trp Asp Tyr Cys Pro Ile Ser Arg Cys
450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Ile Gly Trp Met Val Ser Leu Arg Tyr Arg Asn Lys His
```

500             505             510
Ile Cys Gly Gly Ser Leu Ile Lys Glu Ser Trp Val Leu Thr Ala Arg
            515             520             525

Gln Cys Phe Pro Ser Arg Asp Leu Lys Asp Tyr Glu Ala Trp Leu Gly
        530             535             540

Ile His Asp Val His Gly Arg Gly Asp Glu Lys Cys Lys Gln Val Leu
545             550             555             560

Asn Val Ser Gln Leu Val Tyr Gly Pro Glu Gly Ser Asp Leu Val Leu
            565             570             575

Met Lys Leu Ala Arg Pro Ala Val Leu Asp Asp Phe Val Ser Thr Ile
        580             585             590

Asp Leu Pro Asn Tyr Gly Cys Thr Ile Pro Glu Lys Thr Ser Cys Ser
            595             600             605

Val Tyr Gly Trp Gly Tyr Thr Gly Leu Ile Asn Tyr Asp Gly Leu Leu
        610             615             620

Arg Val Ala His Leu Tyr Ile Met Gly Asn Glu Lys Cys Ser Gln His
625             630             635             640

His Arg Gly Lys Val Thr Leu Asn Glu Ser Glu Ile Cys Ala Gly Ala
            645             650             655

Glu Lys Ile Gly Ser Gly Pro Cys Glu Gly Asp Tyr Gly Gly Pro Leu
        660             665             670

Val Cys Glu Gln His Lys Met Arg Met Val Leu Gly Val Ile Val Pro
            675             680             685

Gly Arg Gly Cys Ala Ile Pro Asn Arg Pro Gly Ile Phe Val Arg Val
        690             695             700

Ala Tyr Tyr Ala Lys Trp Ile His Lys Ile Ile Leu Thr Tyr Lys Val
705             710             715             720

Pro Gln Ser

<210> SEQ ID NO 3
<211> LENGTH: 7113
<212> TYPE: DNA
<213> ORGANISM: Artificial Sequence
<220> FEATURE:
<223> OTHER INFORMATION: nucleotide sequence of hybrid HGF

<400> SEQUENCE: 3

| | | | | | | |
|---|---|---|---|---|---|---|
| atgtgggtga | ccaaactcct | gccagccctg | ctgctgcagc | atgtcctcct | gcatctcctc | 60 |
| ctgctcccca | tcgccatccc | ctatgcagag | ggacaaagga | aaagaagaaa | tacaattcat | 120 |
| gaattcaaaa | aatcagcaaa | gactacccta | atcaaaatag | atccagcact | gaagataaaa | 180 |
| accaaaaaag | tgaatactgc | agaccaatgt | gctaatagat | gtactaggaa | taaaggactt | 240 |
| ccattcactt | gcaaggcttt | tgtttttgat | aaagcaagaa | acaatgcct | ctggttcccc | 300 |
| ttcaatagca | tgtcaagtgg | agtgaaaaaa | gaatttggcc | atgaatttga | cctctatgaa | 360 |
| aacaaagact | acattagaaa | ctgcatcatt | ggtaaaggac | gcagctacaa | gggaacagta | 420 |
| tctatcacta | agagtggcat | caaatgtcag | ccctggagtt | ccatgatacc | acacgaacac | 480 |
| aggtaagaac | agtatgaaga | aaagagatga | agcctctgtc | ttttttacat | gttaacagtc | 540 |
| tcatattagt | ccttcagaat | aattctacaa | tcctaaaata | acttagccaa | cttgctgaat | 600 |
| tgtattacgg | caaggtttat | atgaattcat | gactgatatt | tagcaaatga | ttaattaata | 660 |
| tgttaataaa | atgtagccaa | aacaatatct | taccttaatg | cctcaatttg | tagatctcgg | 720 |
| tatttgtgaa | ataataacgt | aaacttcgtt | taaaaggatt | cttcttcctg | tctttgagaa | 780 |

```
agtacggcac tgtgcagggg gagaggttga ttgtgaaaaa tcagaggtag atgagaatct      840
tactgagggc tgagggttct ttaaccttgg tggatctcaa cattggttgc acattaaaat      900
cacctgctgc aagcccttga cgaatcttac ttagaagatg acaacacaga acaattaaat      960
cagaatctct ggggagaata gggcaccagt attttttgag ctcccaccat gattccaaag     1020
tgcagccaaa tttgagaacc actgctaaaa gctcaagctt cagattgacc agcttttcca     1080
tctcacctat cgcctaaaga ccaaattgga taaatgtgtt cattacgaca gatgggtact     1140
atttaaagat gagtaaacac aatatactta ggctcgtcag actgagagtt ttaatcatca     1200
ctgaggaaaa acatagatat ctaatactga ctggagtatt agtcaaggct tatttcacac     1260
acaattttat cagaaaccaa agtagtttaa aacagctctc cccttattag taatgcattg     1320
gagggtttac tttaccatgt accttgctga gcactgtacc ttgttaatct catttacttg     1380
taatgagaac cacacagcgg gtagttttat tggttctatt ttacctacat gacaaaactg     1440
aagcataaaa acacttagta agttttcagt gtcatgcaca actaggaagt gacatggcca     1500
gaatataagc ccagtcacca tcactctata acctgcgctt ttaacaactt cagggcatga     1560
cacatttggc cggtcagtag aacccatgct gtgatttgtt tttgcagtgg tggtgatgac     1620
tgccttgttg aatccacttt ttattctatt ccattttggg gacacaattc tgcaagatga     1680
ttcttcatta ggaaacagag atgagttatt gaccaacaca gaaagaaaaa gagtttgttg     1740
ctccacactg ggattaaacc tatgatcttg gcctaattaa cactagctag taagtgtcca     1800
agctgatcat ctctacaaca tttcaataac agaaaacaac aattttcaaa attagttact     1860
tacaattatg tagaaatgcc tctaaaacac agtattttcc ttatattaca aaaacaaaaa     1920
ttataattgg ttttgtcctc ttttgagagt ttgcatggtg ttactccctg catagtgaag     1980
aaaacatttt atttaagtag atggatctaa gttttttcatg aacaaaggaa tgacatttga     2040
aatcaatcct accctagtcc aggagaatgc attagattaa cctagtagag gtcttatttc     2100
accctgagtt ttctatgatc gtgattctct gctggaggag taattgtgaa atagatctct     2160
ctgggaactg gcttcctagt ccaatcagct cttttaccaa tgaacacttc cttgtgatat     2220
agatgtttat ggccgagagg atccagtata ttaataaaat ccctttttgt attcaatgag     2280
ggaaacacat aattttcatc aattagcagc ttattggaat atctgcatga tggtttaaca     2340
cttttaagtg ttgactaaag attaatttta cagaaaatag aaaaagaaat atgtttctgt     2400
ctggaggaat gatttattgt tgaccctaa attgaaatat tttactagtg gcttaatgga     2460
aagatgatga aagatgatga aattaatgta gaagcttaac tagaaaatca ggtgacctga     2520
tatctacatc tgtatccttc attggccacc cagcattcat taatgaatca gatgatggaa     2580
tagatcaagt ttcctaggaa cacagtgaat attaaaagaa aacaaaggga gcctagcacc     2640
tagaagacct agtttatatt tcaaagtata tttggatgta acccaatttt aaacatttcc     2700
tcacttgtct ctcttaaagc cttgccaaca gcaaggacag agaaccaaaa atagtgtata     2760
tatgaataaa tgcttattac agaatctgct gactggcaca tgctttgtgt gtaatgggtt     2820
ctcataaaca cttgttgaat gaacacacat aagtgaaaga gcatggctag gcttcatccc     2880
ttggtcaaat atggggtgct aaagaaaagc agggaaata cattgggaca ctaacaaaaa     2940
aaaacagtta atttaggtaa aagataaaat acaccacaga atgaagaaaa gagatgaccc     3000
agactgctct ttaaccttca tgtcctagag aggtttttga tatgaattgc attcagaatt     3060
gtggaaagga gcccatcttt tctcttcatt ttgattttat taactccaat ggggaattt      3120 tattcgtgtt ttggccatat ctactttga tttctacatt attctctctt cctttctacc     3180
```

```
tgtatttgtc ctaataaatt gttgacttat taattcacta cttcctcaca gcttttttt    3240 ggctttacaa atccactgga aaggtatatg ggtgtatcac tttgtgtatt tcggtgtgca    3300
tgtgtagagg ggacaaaaat cctctctcaa actataaata ttgagtattt gtgtattgaa    3360
catttgctat aactactagg tttcttaaat aatcttaata tataaaatga tatagaaaaa    3420
gggaaattat agttcgtatt attcatctaa gtgaagagat taaaacccag ggagtaaata    3480
aattgtctaa ggactaaggt tgtatactat ttaggtgata gatatggggc aaccgtatgg    3540
gttttatgat taacaaataa acttctcacc actctaccat atcaactttt ccataaaaga    3600
gagctatagt attctttgct taaataaatt tgattagtgc atgacttctt gaaaacatat    3660
aaagcaaaag tcacatttga ttctatcaga aaagtgagta agccatggcc caaacaaaag    3720
atgcattaaa atattctgga atgatggagc taaaagtaag aaaaatgact ttttaaaaaa    3780
gtttactgtt aggaattgtg aaattatgct gaattttagt tgcattataa ttttttgtcag   3840 tcatacggtc tgacaacctg tcttatttct atttccccat atgaggaatg ctagttaagt    3900
atggatatta actattacta cttagatgca ttgaagttgc ataatatgga taatacttca    3960
ctggttccct gaaaatgttt agttagtaat aagtctctta cactatttgt tttgtccaat    4020
aatttatatt ttctgaagac ttaactctag aatacactca tgtcaaaatg aaagaatttc    4080
attgcaaaat attgcttggt acatgacgca tacctgtatt tgttttgtgt cacaacatga    4140
aaaatgatgg tttattagaa gtttcattgg gtaggaaaca catttgaatg gtatttacta    4200
agatactaaa atccttggac ttcactctaa ttttagtgcc atttagaact caaggtctca    4260
gtaaaagtag aaataaagcc tgttaacaaa acacaagctg aatattaaaa atgtaactgg    4320 atttttcaaag aaatgtttac tggtattacc tgtagatgta tattctttat tatgatcttt   4380
tgtgtaaagt ctggcagaca aatgcaatat ctaattgttg agtccaatat cacaagcagt    4440
acaaaagtat aaaaaagact tggccttttc taatgtgtta aaatacttta tgctggtaat    4500
aacactaaga gtagggcact agaaatttta agtgaagata atgtgttgca gttactgcac    4560
tcaatggctt actattataa accaaaactg ggatcactaa gctccagtca gtcaaaatga    4620
tcaaaattat tgaagagaat aagcaattct gttctttatt aggacacagt agatacagac    4680
tacaaagtgg agtgtgctta ataagaggta gcatttgtta agtgtcaatt actctattat    4740
cccttggagc ttctcaaaat aaccatataa ggtgtaagat gttaaaggtt atggttacac    4800
tcagtgcaca ggtaagctaa taggctgaga gaagctaaat tacttactgg ggtctcacag    4860
taagaaagtg agctgaagtt tcagcccaga tttaactgga ttctgggctc tttattcatg    4920
ttacttcatg aatctgtttc tcaattgtgc agaaaaaagg gggctattta taagaaaagc    4980
aataaacaaa caagtaatga tctcaaataa gtaatgcaag aaatagtgag atttcaaaat    5040
cagtggcagc gatttctcag ttctgtccta agtggccttg ctcaatcacc tgctatcttt    5100
tagtggagct ttgaaattat gtttcagaca acttcgattc agttctagaa tgtttgactc    5160
agcaaattca caggctcatc tttctaactt gatggtgaat atggaaattc agctaaatgg    5220
atgttaataa aattcaaacg ttttaaggac agatgaaaat gacagaattt taaggtaaaa    5280
tatatgaagg aatataagat aaaggatttt tctaccttca gcaaaaacat acccactaat    5340
tagtaaaatt aataggcaaa aaaaagttgc atgctcttat actgtaatga ttatcatttt    5400
aaaactagct ttttgccttc gagctatcgg ggtaaagacc tacaggaaaa ctactgtcga    5460
aatcctcgag gggaagaagg gggaccctgg tgtttcacaa gcaatccaga ggtacgctac    5520
```

```
gaagtctgtg acattcctca gtgttcagaa gttgaatgca tgacctgcaa tggggagagt    5580
tatcgaggtc tcatggatca tacagaatca ggcaagattt gtcagcgctg ggatcatcag    5640
acaccacacc ggcacaaatt cttgcctgaa agatatcccg acaagggctt tgatgataat    5700
tattgccgca atcccgatgg ccagccgagg ccatggtgct atactcttga ccctcacacc    5760
cgctgggagt actgtgcaat aaaacatgc gctgacaata ctatgaatga cactgatgtt    5820
cctttggaaa caactgaatg catccaaggt caaggagaag gctacagggg cactgtcaat    5880
accatttgga atggaattcc atgtcagcgt tgggattctc agtatcctca cgagcatgac    5940
atgactcctg aaaatttcaa gtgcaaggac ctacgagaaa attactgccg aaatccagat    6000
gggtctgaat caccctggtg ttttaccact gatccaaaca tccgagttgg ctactgctcc    6060
caaattccaa actgtgatat gtcacatgga caagattgtt atcgtgggaa tggcaaaaat    6120
tatatgggca acttatccca acaagatct ggactaacat gttcaatgtg ggacaagaac    6180
atggaagact acatcgtca tatcttctgg gaaccagatg caagtaagct gaatgagaat    6240
tactgccgaa atccagatga tgatgctcat ggaccctggt gctacacggg aaatccactc    6300
attccttggg attattgccc tatttctcgt tgtgaaggtg ataccacacc tacaatagtc    6360
aatttagacc atcccgtaat atcttgtgcc aaaacgaaac aattgcgagt tgtaaatggg    6420
attccaacac gaacaaacat aggatggatg gttagtttga gatacagaaa taaacatatc    6480
tgcggaggat cattgataaa ggagagttgg gttcttactg cacgacagtg tttcccttct    6540
cgagacttga agattatga agcttggctt ggaattcatg atgtccacgg aagaggagat    6600
gagaaatgca acaggttct caatgtttcc cagctggtat atggccctga aggatcagat    6660
ctggttttaa tgaagcttgc caggcctgct gtcctggatg attttgttag tacgattgat    6720
ttacctaatt atggatgcac aattcctgaa aagaccagtt gcagtgttta tggctggggc    6780
tacactggat tgatcaacta tgatggccta ttacgagtgg cacatctcta taatgggga    6840 aatgagaaat gcagccagca tcatcgaggg aaggtgactc tgaatgagtc tgaaatatgt    6900
gctggggctg aaaagattgg atcaggacca tgtgaggggg attatggtgg cccacttgtt    6960
tgtgagcaac ataaaatgag aatggttctt ggtgtcattg ttcctggtcg tggatgtgcc    7020
attccaaatc gtcctggtat ttttgtccga gtagcatatt atgcaaaatg gatacacaaa    7080
attattttaa catataaggt accacagtca tag                                 7113
```

<210> SEQ ID NO 4
<211> LENGTH: 6190
<212> TYPE: DNA
<213> ORGANISM: Artificial Sequence
<220> FEATURE:
<223> OTHER INFORMATION: nucleotide sequence of HGF-X2

<400> SEQUENCE: 4

```
atgtgggtga ccaaactcct gccagccctg ctgctgcagc atgtcctcct gcatctcctc      60
ctgctcccca tcgccatccc ctatgcagag ggacaaagga aaagaagaaa tacaattcat     120
gaattcaaaa aatcagcaaa gactacccta atcaaaatag atccagcact gaagataaaa     180
accaaaaaag tgaatactgc agaccaatgt gctaatagat gtactaggaa taagggactt     240
ccattcactt gcaaggcttt tgtttttgat aaagcaagaa acaatgcct ctggttcccc     300 ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta gagtggcat caaatgtcag ccctggagtt ccatgatacc acacgaacac     480
```

```
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa aacaatatct taccttaatg cctcaatttg tagatctcgg    720
tatttgtgaa ataataacgt aaacttcgtt taaaaggatt cttcttcctg tctttgagaa    780
agtacggcac tgtgcagggg gagaggttga ttgtgaaaaa tcagaggtag atgagaatct    840
tactgagggc tgagggttct ttaaccttgg tggatctcaa cattggttgc acattaaaat    900
cacctgctgc aagcccttga cgaatcttac ttagaagatg acaacacaga acaattaaat    960
cagaatctct ggggagaata gggcaccagt attttttgag ctcccaccat gattccaaag   1020
tgcagccaaa tttgagaacc actgctaaaa gctcaagctt cagattgacc agcttttcca   1080
tctcacctat cgcctaaaga ccaaattgga taaatgtgtt cattacgaca gatgggtact   1140
atttaaagat gagtaaacac aatatactta ggctcgtcag actgagagtt ttaatcatca   1200
ctgaggaaaa acatagatat ctaatactga ctggagtatt agtcaaggct tatttcacac   1260
acaattttat cagaaaccaa agtagttaa aacagctctc cccttattag taatgcattg   1320
gagggtttac tttaccatgt accttgctga gcactgtacc ttgttaatct catttacttg   1380
taatgagaac cacacagcgg gtagttttat tggttctatt ttacctacat gacaaaactg   1440
aagcataaaa acacttagta agttttcagt gtcatgcaca actaggaagt gacatggcca   1500
gaatataagc ccagtcacca tcactctata acctgcgctt ttaacaactt cagggcatga   1560
cacatttggc cggtcagtag aacccatgct gtgatttgtt tttgcagtgg tggtgatgac   1620
tgccttgttg aatccacttt ttattctatt ccattttggg gacacaattc tgcaagatga   1680
ttcttcatta ggaaacagag atgagttatt gaccaacaca gaaagaaaaa gagtttgttg   1740
ctccacactg ggattaaacc tatgatcttg gcctaattaa cactagctag taagtgtcca   1800
agctgatcat ctctacaaca tttcaataac agaaaacaac aattttcaaa attagttact   1860
tacaattatg tagaaatgcc tctaaaacac agtattttcc ttatattaca aaaacaaaaa   1920
ttataattgg ttttgtcctc ttttgagagt ttgcatggtg ttactccctg catagtgaag   1980
aaaacatttt atttaagtag atggatctaa gttttttcatg aacaaaggaa tgacatttga   2040
aatcaatcct accctagtcc aggagaatgc attagattaa cctagtagag gtcttatttc   2100
accctgagtt ttctatgatc gtgattctct gctggaggag taattgtgaa atagatctct   2160
ctgggaactg gcttcctagt ccaatcagct cttttaccaa tgaacacttc cttgtgatat   2220
agatgtttat ggccgagagg atcccttcct ttctacctgt atttgtccta ataaattgtt   2280
gacttattaa ttcactactt cctcacagct ttttttggc tttacaaatc cactggaaag   2340
gtatatgggt gtatcacttt gtgtatttcg gtgtgcatgt gtagagggga caaaaatcct   2400
ctctcaaact ataaatattg agtatttgtg tattgaacat ttgctataac tactaggttt   2460
cttaaataat cttaatatat aaaatgatat agaaaaggg aattatagt tcgtattatt   2520 catctaagtg aagagattaa aacccaggga gtaaataaat tgtctaagga ctaaggttgt   2580
atactattta ggtgatagat atggggcaac cgtatgggtt ttatgattaa caaataaact   2640
tctcaccact ctaccatatc aacttttcca taaagagag ctatagtatt ctttgcttaa   2700
ataaatttga ttagtgcatg acttcttgaa aacatataaa gcaaagtca catttgattc   2760 tatcagaaaa gtgagtaagc catggcccaa acaaaagatg cattaaaata ttctggaatg   2820
```

-continued

```
atggagctaa aagtaagaaa aatgactttt taaaaaagtt tactgttagg aattgtgaaa    2880
ttatgctgaa ttttagttgc attataattt ttgtcagtca tacggtctga caacctgtct    2940
tatttctatt tccccatatg aggaatgcta gttaagtatg gatattaact attactactt    3000
agatgcattg aagttgcata atatggataa tacttcactg gttccctgaa aatgtttagt    3060
tagtaataag tctcttacac tatttgtttt gtccaataat ttatattttc tgaagactta    3120
actctagaat acactcatgt caaaatgaaa gaatttcatt gcaaaatatt gcttggtaca    3180
tgacgcatac ctgtatttgt tttgtgtcac aacatgaaaa atgatggttt attagaagtt    3240
tcattgggta ggaaacacat ttgaatggta tttactaaga tactaaaatc cttggacttc    3300
actctaattt tagtgccatt tagaactcaa ggtctcagta aaagtagaaa taaagcctgt    3360
taacaaaaca caagctgaat attaaaaatg taactggatt ttcaaagaaa tgtttactgg    3420
tattacctgt agatgtatat tctttattat gatcttttgt gtaaagtctg gcagacaaat    3480
gcaatatcta attgttgagt ccaatatcac aagcagtaca aaagtataaa aaagacttgg    3540
cctttttctaa tgtgttaaaa tactttatgc tggtaataac actaagagta gggcactaga    3600
aattttaagt gaagataatg tgttgcagtt actgcactca atggcttact attataaacc    3660
aaaactggga tcactaagct ccagtcagtc aaaatgatca aaattattga agagaataag    3720
caattctgtt ctttattagg acacagtaga tacagactac aaagtggagt gtgcttaata    3780
agaggtagca tttgttaagt gtcaattact ctattatccc ttggagcttc tcaaaataac    3840
catataaggt gtaagatgtt aaaggttatg gttacactca gtgcacaggt aagctaatag    3900
gctgagagaa gctaaattac ttactggggt ctcacagtaa gaaagtgagc tgaagtttca    3960
gcccagattt aactggattc tgggctcttt attcatgtta cttcatgaat ctgtttctca    4020
attgtgcaga aaaagggggg ctattttataa gaaaagcaat aaacaaacaa gtaatgatct    4080
caaataagta atgcaagaaa tagtgagatt tcaaaatcag tggcagcgat ttctcagttc    4140
tgtcctaagt ggccttgctc aatcacctgc tatcttttag tggagctttg aaattatgtt    4200
tcagacaact tcgattcagt tctagaatgt ttgactcagc aaattcacag gctcatcttt    4260
ctaacttgat ggtgaaatatg gaaattcagc taaatggatg ttaataaaat tcaaacgttt    4320
taaggacaga tgaaaatgac agaattttaa ggtaaaatat atgaaggaat ataagataaa    4380
ggattttct accttcagca aaaacatacc cactaattag taaaattaat aggcaaaaaa    4440
aagttgcatg ctcttatact gtaatgatta tcattttaaa actagctttt tgccttcgag    4500
ctatcggggt aaagacctac aggaaaacta ctgtcgaaat cctcgagggg aagaaggggg    4560
accctggtgt ttcacaagca atccagaggt acgctacgaa gtctgtgaca ttcctcagtg    4620
ttcagaagtt gaatgcatga cctgcaatgg ggagagttat cgaggtctca tggatcatac    4680
agaatcaggc aagatttgtc agcgctggga tcatcagaca ccacaccggc acaaattctt    4740
gcctgaaaga tatcccgaca agggctttga tgataattat tgccgcaatc ccgatggcca    4800
gccgaggcca tggtgctata ctcttgaccc tcacacccgc tgggagtact gtgcaattaa    4860
aacatgcgct gacaatacta tgaatgacac tgatgttcct ttggaaacaa ctgaatgcat    4920
ccaaggtcaa ggagaaggct acaggggcac tgtcaatacc atttggaatg gaattccatg    4980
tcagcgttgg gattctcagt atcctcacga gcatgacatg actcctgaaa atttcaagtg    5040
caaggaccta cgagaaaatt actgccgaaa tccagatggg tctgaatcac cctggtgttt    5100
taccactgat ccaaacatcc gagttggcta ctgctcccaa attccaaact gtgatatgtc    5160
acatggacaa gattgttatc gtgggaatgg caaaaattat atgggcaact tatcccaaac    5220
```

| | | |
|---|---|---|
| aagatctgga ctaacatgtt caatgtggga caagaacatg gaagacttac atcgtcatat | 5280 |
| cttctgggaa ccagatgcaa gtaagctgaa tgagaattac tgccgaaatc cagatgatga | 5340 |
| tgctcatgga ccctggtgct acacgggaaa tccactcatt ccttgggatt attgccctat | 5400 |
| ttctcgttgt gaaggtgata ccacacctac aatagtcaat ttagaccatc ccgtaatatc | 5460 |
| ttgtgccaaa acgaaacaat tgcgagttgt aaatgggatt ccaacacgaa caaacatagg | 5520 |
| atggatggtt agtttgagat acagaaataa acatatctgc ggaggatcat tgataaagga | 5580 |
| gagttgggtt cttactgcac gacagtgttt cccttctcga gacttgaaag attatgaagc | 5640 |
| ttggcttgga attcatgatg tccacggaag aggagatgag aaatgcaaac aggttctcaa | 5700 |
| tgtttcccag ctggtatatg ccctgaagg atcagatctg gttttaatga agcttgccag | 5760 |
| gcctgctgtc ctgatgatt ttgttagtac gattgattta cctaattatg gatgcacaat | 5820 |
| tcctgaaaag accagttgca gtgtttatgg ctggggctac actggattga tcaactatga | 5880 |
| tggcctatta cgagtggcac atctctatat aatgggaaat gagaaatgca gccagcatca | 5940 |
| tcgagggaag gtgactctga atgagtctga aatatgtgct ggggctgaaa agattggatc | 6000 |
| aggaccatgt gagggggatt atggtggccc acttgtttgt gagcaacata aaatgagaat | 6060 |
| ggttcttggt gtcattgttc ctggtcgtgg atgtgccatt ccaaatcgtc ctggtatttt | 6120 |
| tgtccgagta gcatattatg caaaatggat acacaaaatt attttaacat ataaggtacc | 6180 |
| acagtcatag | 6190 |

<210> SEQ ID NO 5
<211> LENGTH: 5190
<212> TYPE: DNA
<213> ORGANISM: Artificial Sequence
<220> FEATURE:
<223> OTHER INFORMATION: nucleotide sequence of HGF-X3

<400> SEQUENCE: 5

| | | |
|---|---|---|
| atgtgggtga ccaaactcct gccagccctg ctgctgcagc atgtcctcct gcatctcctc | 60 |
| ctgctcccca tcgccatccc ctatgcagag ggacaaagga aaagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaaggactt | 240 |
| ccattcactt gcaaggcttt tgttttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggca gcagctacaa gggaacagta | 420 |
| tctatcacta agagtggcat caaatgtcag ccctggagtt ccatgatacc acacgaacac | 480 |
| aggtaagaac agtatgaaga aaagagatga agcctctgtc tttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa acaatatct taccttaatg cctcaatttg tagatctcgg | 720 |
| tatttgtgaa ataataacgt aaacttcgtt taaaaggatt cttcttcctg tctttgagaa | 780 |
| agtacggcac tgtgcagggg gagaggttga ttgtgaaaaa tcagaggtag atgagaatct | 840 |
| tactgagggc tgagggttct ttaacccttgg tggatctcaa cattggttgc acattaaaat | 900 |
| cacctgctgc aagcccttga cgaatcttac ttagaagatg acaacacaga acaattaaat | 960 |
| cagaatctct ggggagaata gggcaccagt attttttgag ctcccaccat gattccaaag | 1020 |

```
tgcagccaaa tttgagaacc actgctaaaa gctcaagctt cagattgacc agcttttcca    1080
tctcacctat cgcctaaaga ccaaattgga taaatgtgtt cattacgaca gatgggtact    1140
atttaaagat gagtaaacac aatatactta ggctcgtcag actgagagtt ttaatcatca    1200
ctgaggaaaa acatagatat ctaatactga ctggagtatt agtcaaggct tatttcacac    1260 acaatttat cagaaaccaa agtagtttaa aacagctctc cccttattag taatgcattg     1320
gagggtttac tttaccatgt accttgctga gcactgtacc ttgttaatct catttacttg    1380
taatgagaac cacacagcgg gtagttttat tggttctatt ttacctacat gacaaaactg    1440
aagcataaaa acacttagta agttttcagt gtcatgcaca actaggaagt gacatggcca    1500
gaatataagc ccagtcacca tcactctata acctgcgctt ttaacaactt cagggcatga    1560
cacatttggc cggtcagtag aacccatgct gtgatttgtt tttgcagtgg tggtgatgac    1620
tgccttgttg aatccacttt ttattctatt ccatttgggg acacaattc tgcaagatga     1680 ttcttcatta ggaaacagag atgagttatt gaccaacaca gaaagaaaaa gagtttgttg    1740
ctccacactg ggattaaacc tatgatcttg gcctaattaa cactagctag taagtgtcca    1800
agctgatcat ctctacaaca tttcaataac agaaaacaac aattttcaaa attagttact    1860
tacaattatg tagaaatgcc tctaaaacac agtattttcc ttatattaca aaacaaaaa    1920 ttataattgg ttttgtcctc ttttgagagt ttgcatggtg ttactccctg catagtgaag    1980
aaaacatttt atttaagtag atggatctaa gtttttcatg aacaaggaa tgacatttga     2040 aatcaatcct accctagtcc aggagaatgc attagattaa cctagtagag gtcttatttc    2100
accctgagtt ttcatgatc gtgattctct gctggaggag taattgtgaa atagatctct     2160
ctgggaactg gcttcctagt ccaatcagct cttttaccaa tgaacacttc cttgtgatat    2220
agatgtttat ggccgagagg atcctgggta ggaaacacat ttgaatggta tttactaaga    2280
tactaaaatc cttggacttc actctaattt tagtgccatt tagaactcaa ggtctcagta    2340
aaagtagaaa taaagcctgt taacaaaaca caagctgaat attaaaaatg taactggatt    2400
ttcaaagaaa tgtttactgg tattacctgt agatgtatat tctttattat gatcttttgt    2460
gtaaagtctg gcagacaaat gcaatatcta attgttgagt ccaatatcac aagcagtaca    2520
aaagtataaa aaagacttgg cctttttctaa tgtgttaaaa tactttatgc tggtaataac    2580
actaagagta gggcactaga aattttaagt gaagataatg tgttgcagtt actgcactca    2640
atggcttact attataaacc aaaactggga tcactaagct ccagtcagtc aaaatgatca    2700
aaattattga agagaataag caattctgtt ctttattagg acacagtaga tacagactac    2760
aaagtggagt gtgcttaata agaggtagca tttgttaagt gtcaattact ctattatccc    2820
ttggagcttc tcaaaataac catataaggt gtaagatgtt aaaggttatg gttacactca    2880
gtgcacaggt aagctaatag gctgagagaa gctaaattac ttactggggt ctcacagtaa    2940
gaaagtgagc tgaagtttca gcccagattt aactggattc tgggctcttt attcatgtta    3000
cttcatgaat ctgtttctca attgtgcaga aaaagggggg ctatttataa gaaaagcaat    3060
aaacaaacaa gtaatgatct caaataagta atgcaagaaa tagtgagatt tcaaaatcag    3120
tggcagcgat ttctcagttc tgtcctaagt ggccttgctc aatcacctgc tatctttag     3180 tggagctttg aaattatgtt tcagacaact tcgattcagt tctagaatgt ttgactcagc    3240
aaattcacag gctcatcttt ctaacttgat ggtgaatatg gaaattcagc taaatggatg    3300
ttaataaaat tcaacgtttt taaggacaga tgaaaatgac agaattttaa ggtaaaatat    3360
atgaaggaat ataagataaa ggatttttct accttcagca aaaacatacc cactaattag    3420
```

| | | |
|---|---|---|
| taaaattaat aggcaaaaaa aagttgcatg ctcttatact gtaatgatta tcattttaaa | 3480 | |
| actagctttt tgccttcgag ctatcggggt aaagacctac aggaaaacta ctgtcgaaat | 3540 | |
| cctcgagggg aagaagggggg accctggtgt ttcacaagca atccagaggt acgctacgaa | 3600 | |
| gtctgtgaca ttcctcagtg ttcagaagtt gaatgcatga cctgcaatgg ggagagttat | 3660 | |
| cgaggtctca tggatcatac agaatcaggc aagatttgtc agcgctggga tcatcagaca | 3720 | |
| ccacaccggc acaaattctt gcctgaaaga tatcccgaca agggctttga tgataattat | 3780 | |
| tgccgcaatc ccgatggcca gccgaggcca tggtgctata ctcttgaccc tcacacccgc | 3840 | |
| tgggagtact gtgcaattaa acatgcgct gacaatacta tgaatgacac tgatgttcct | 3900 | |
| ttggaaacaa ctgaatgcat ccaaggtcaa ggagaaggct acaggggcac tgtcaatacc | 3960 | |
| atttggaatg gaattccatg tcagcgttgg gattctcagt atcctcacga gcatgacatg | 4020 | |
| actcctgaaa atttcaagtg caaggaccta cgagaaaatt actgccgaaa tccagatggg | 4080 | |
| tctgaatcac cctggtgttt taccactgat ccaaacatcc gagttggcta ctgctcccaa | 4140 | |
| attccaaact gtgatatgtc acatggacaa gattgttatc gtgggaatgg caaaaattat | 4200 | |
| atgggcaact tatcccaaac aagatctgga ctaacatgtt caatgtggga caagaacatg | 4260 | |
| gaagacttac atcgtcatat cttctgggaa ccagatgcaa gtaagctgaa tgagaattac | 4320 | |
| tgccgaaatc cagatgatga tgctcatgga ccctggtgct acgggaaa tccactcatt | 4380 | |
| ccttgggatt attgccctat ttctcgttgt gaaggtgata ccacacctac aatagtcaat | 4440 | |
| ttagaccatc ccgtaatatc ttgtgccaaa acgaaacaat tgcgagttgt aaatgggatt | 4500 | |
| ccaacacgaa caaacatagg atggatggtt agtttgagat acagaaataa acatatctgc | 4560 | |
| ggaggatcat tgataaagga gagttgggtt cttactgcac gacagtgttt cccttctcga | 4620 | |
| gacttgaaag attatgaagc ttggcttgga attcatgatg tccacggaag aggagatgag | 4680 | |
| aaatgcaaac aggttctcaa tgtttcccag ctggtatatg gccctgaagg atcagatctg | 4740 | |
| gttttaatga agcttgccag gcctgctgtc ctggatgatt ttgttagtac gattgattta | 4800 | |
| cctaattatg gatgcacaat tcctgaaaag accagttgca gtgtttatgg ctggggctac | 4860 | |
| actgattga tcaactatga tggcctatta cgagtggcac atctctatat aatgggaaat | 4920 | |
| gagaaatgca gccagcatca tcgagggaag gtgactctga atgagtctga aatatgtgct | 4980 | |
| ggggctgaaa agattggatc aggaccatgt gaggggggatt atggtggccc acttgtttgt | 5040 | |
| gagcaacata aaatgagaat ggttcttggt gtcattgttc ctggtcgtgg atgtgccatt | 5100 | |
| ccaaatcgtc ctggtatttt tgtccgagta gcatattatg caaaatggat acacaaaatt | 5160 | |
| attttaacat ataaggtacc acagtcatag | 5190 | |

<210> SEQ ID NO 6
<211> LENGTH: 4241
<212> TYPE: DNA
<213> ORGANISM: Artificial Sequence
<220> FEATURE:
<223> OTHER INFORMATION: nucleotide sequence of HGF-X4

<400> SEQUENCE: 6

| | |
|---|---|
| atgtgggtga ccaaactcct gccagccctg ctgctgcagc atgtcctcct gcatctcctc | 60 |
| ctgctccca tcgccatccc ctatgcagag ggacaaagga aagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaggactt | 240 |

```
ccattcactt gcaaggcttt tgtttttgat aaagcaagaa aacaatgcct ctggttcccc    300
ttcaatagca tgtcaagtgg agtgaaaaaa gaatttggcc atgaatttga cctctatgaa    360
aacaaagact acattagaaa ctgcatcatt ggtaaaggac gcagctacaa gggaacagta    420
tctatcacta agagtggcat caaatgtcag ccctggagtt ccatgatacc acacgaacac    480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa aacaatatct taccttaatg cctcaatttg tagatctcgg    720
tatttgtgaa ataataacgt aaacttcgtt taaaaggatt cttcttcctg tctttgagaa    780
agtacggcac tgtgcagggg gagaggttga ttgtgaaaaa tcagaggtag atgagaatct    840
tactgagggc tgagggttct ttaaccttgg tggatctcaa cattggttgc acattaaaat    900
cacctgctgc aagcccttga cgaatcttac ttagaagatg acaacacaga acaattaaat    960
cagaatctct ggggagaata gggcaccagt attttttgag ctcccaccat gattccaaag   1020
tgcagccaaa tttgagaacc actgctaaaa gctcaagctt cagattgacc agcttttcca   1080
tctcacctat cgcctaaaga ccaaattgga taaatgtgtt cattacgaca gatgggtact   1140
atttaaagat gagtaaacac aatatactta ggctcgtcag actgagagtt ttaatcatca   1200
ctgaggaaaa acatagatat ctaatactga ctggagtatt agtcaaggct tatttcacac   1260
acaattttat cagaaaccaa agtagtttaa aacagctctc cccttattag taatgcattg   1320
gagggtttac tttaccatgt accttgctga gcactgtacc ttgttaatct catttacttg   1380
taatgagaac cacacagcgg gtagttttat tggttctatt ttacctacat gacaaaactg   1440
aagcataaaa acacttagta agttttcagt gtcatgcaca actaggaagt gacatggcca   1500
gaatataagc ccagtcacca tcactctata acctgcgctt ttaacaactt cagggcatga   1560
cacatttggc cggtcagtag aacccatgct gtgatttgtt tttgcagtgg tggtgatgac   1620
tgccttgttg aatccacttt ttattctatt ccattttggg gacacaattc tgcaagatga   1680
ttcttcatta ggaaacagag atgagttatt gaccaacaca gaaagaaaaa gagtttgttg   1740
ctccacactg ggattaaacc tatgatcttg gcctaattaa cactagctag taagtgtcca   1800
agctgatcat ctctacaaca tttcaataac agaaaacaac aattttcaaa attagttact   1860
tacaattatg tagaaatgcc tctaaaacac agtattttcc ttatattaca aaaacaaaaa   1920
ttataattgg ttttgtcctc ttttgagagt ttgcatggtg ttactccctg catagtgaag   1980
aaaacatttt atttaagtag atggatctaa gttttttcatg aacaaaggaa tgacatttga   2040
aatcaatcct accctagtcc aggagaatgc attagattaa cctagtagag gtcttatttc   2100
accctgagtt ttctatgatc gtgattctct gctggaggag taattgtgaa atagatctct   2160
ctgggaactg gcttcctagt ccaatcagct cttttaccaa tgaacacttc cttgtgatat   2220
agatgtttat ggccgagagg atccttatgt ttcagacaac ttcgattcag ttctagaatg   2280
tttgactcag caaattcaca ggctcatctt tctaacttga tggtgaatat ggaaattcag   2340
ctaaatggat gttaataaaa ttcaaacgtt ttaaggacag atgaaaatga cagaatttta   2400
aggtaaaata tatgaaggaa tataagataa aggattttc taccttcagc aaaaacatac   2460
ccactaatta gtaaaattaa taggcaaaaa aaagttgcat gctcttatac tgtaatgatt   2520
atcattttaa aactagcttt ttgccttcga gctatcgggg taaagaccta caggaaaact   2580
actgtcgaaa tcctcgaggg gaagaagggg gaccctggtg tttcacaagc aatccagagg   2640
```

```
tacgctacga agtctgtgac attcctcagt gttcagaagt tgaatgcatg acctgcaatg      2700
gggagagtta tcgaggtctc atggatcata cagaatcagg caagatttgt cagcgctggg      2760
atcatcagac accacaccgg cacaaattct tgcctgaaag atatcccgac aagggctttg      2820
atgataatta ttgccgcaat cccgatggcc agccgaggcc atggtgctat actcttgacc      2880
ctcacacccg ctgggagtac tgtgcaatta aacatgcgc tgacaatact atgaatgaca       2940
ctgatgttcc tttggaaaca actgaatgca tccaaggtca aggagaaggc tacaggggca      3000
ctgtcaatac catttggaat ggaattccat gtcagcgttg ggattctcag tatcctcacg      3060
agcatgacat gactcctgaa aatttcaagt gcaaggacct acgagaaaat tactgccgaa      3120
atccagatgg gtctgaatca ccctggtgtt ttaccactga tccaaacatc cgagttggct      3180
actgctccca aattccaaac tgtgatatgt cacatggaca agattgttat cgtgggaatg      3240
gcaaaaatta tatgggcaac ttatcccaaa caagatctgg actaacatgt tcaatgtggg      3300
acaagaacat ggaagactta catcgtcata tcttctggga accagatgca agtaagctga      3360
atgagaatta ctgccgaaat ccagatgatg atgctcatgg accctggtgc tacacgggaa      3420
atccactcat tccttgggat tattgcccta tttctcgttg tgaaggtgat accacaccta      3480
caatagtcaa tttagaccat cccgtaatat cttgtgccaa aacgaaacaa ttgcgagttg      3540
taaatgggat tccaacacga acaaacatag gatggatggt tagtttgaga tacagaaata      3600
aacatatctg cggaggatca ttgataaagg agagttgggt tcttactgca cgacagtgtt      3660
tcccttctcg agacttgaaa gattatgaag cttggcttgg aattcatgat gtccacggaa      3720
gaggagatga gaaatgcaaa caggttctca atgtttccca gctggtatat ggccctgaag      3780
gatcagatct ggttttaatg aagcttgcca ggcctgctgt cctggatgat tttgttagta      3840
cgattgattt acctaattat ggatgcacaa ttcctgaaaa accagttgc agtgtttatg       3900 gctgggctaa cactggattg atcaactatg atggcctatt acgagtggca catctctata      3960
taatgggaaa tgagaaatgc agccagcatc atcgagggaa ggtgactctg aatgagtctg      4020
aaatatgtgc tggggctgaa aagattggat caggaccatg tgaggggat tatggtggcc        4080 cacttgtttg tgagcaacat aaaatgagaa tggttcttgg tgtcattgtt cctggtcgtg      4140
gatgtgccat tccaaatcgt cctggtattt ttgtccgagt agcatattat gcaaaatgga      4200
tacacaaaat tattttaaca tataaggtac cacagtcata g                          4241
```

<210> SEQ ID NO 7
<211> LENGTH: 5602
<212> TYPE: DNA
<213> ORGANISM: Artificial Sequence
<220> FEATURE:
<223> OTHER INFORMATION: nucleotide sequence of HGF-X5

<400> SEQUENCE: 7

```
atgtgggtga ccaaactcct gccagccctg ctgctgcagc atgtcctcct gcatctcctc        60
ctgctcccca tcgccatccc ctatgcagag ggacaaagga aagaagaaa tacaattcat       120 gaattcaaaa atcagcaaa gactacccta atcaaaatag atccagcact gaagataaaa       180
accaaaaaag tgaatactgc agaccaatgt gctaatagat gtactaggaa taaaggactt      240
ccattcactt gcaaggcttt tgttttttgat aaagcaagaa acaatgcct ctggttcccc        300 ttcaatagca tgtcaagtgg agtgaaaaaa gaatttggcc atgaatttga cctctatgaa      360
aacaaagact acattagaaa ctgcatcatt ggtaaaggac gcagctacaa gggaacagta      420
```

```
tctatcacta agagtggcat caaatgtcag ccctggagtt ccatgatacc acacgaacac    480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa aacaatatct taccttaatg cctcaatttg tagatctcgg    720
tatttgtgga tccagtatat taataaaatc ccttttttgta ttcaatgagg gaaacacata   780
attttcatca attagcagct tattggaata tctgcatgat ggtttaacac ttttaagtgt    840
tgactaaaga ttaattttac agaaaataga aaagaaata tgtttctgtc tggaggaatg     900
atttattgtt gaccoctaaa ttgaaatatt ttactagtgg cttaatggaa agatgatgaa    960
agatgatgaa attaatgtag aagcttaact agaaaatcag gtgacctgat atctacatct   1020
gtatccttca ttggccaccc agcattcatt aatgaatcag atgatggaat agatcaagtt   1080
tcctaggaac acagtgaata ttaaaagaaa acaaagggag cctagcacct agaagaccta   1140
gtttatattt caaagtatat ttggatgtaa cccaatttta aacatttcct cacttgtctc    1200
tcttaaagcc ttgccaacag caaggacaga gaaccaaaaa tagtgtatat atgaataaat    1260
gcttattaca gaatctgctg actggcacat gctttgtgtg taatgggttc tcataaacac    1320
ttgttgaatg aacacacata agtgaaagag catggctagg cttcatccct tggtcaaata    1380
tggggtgcta aagaaaagca ggggaaatac attgggacac taacaaaaaa aaacagttaa    1440
tttaggtaaa agataaaata caccacagaa tgaagaaaag agatgaccca gactgctctt    1500
taaccttcat gtcctagaga ggttttgat atgaattgca ttcagaattg tggaaaggag    1560
cccatctttt ctcttcattt tgattttatt aactccaatg ggggaatttt attcgtgttt    1620
tggccatatc tacttttgat ttctacatta ttctctcttc ctttctacct gtatttgtcc    1680
taataaattg ttgacttatt aattcactac ttcctcacag cttttttttg gctttacaaa    1740
tccactggaa aggtatatgg gtgtatcact ttgtgtattt cggtgtgcat gtgtagaggg    1800
gacaaaaatc ctctctcaaa ctataaatat tgagtatttg tgtattgaac atttgctata    1860
actactaggt ttcttaaata atcttaatat ataaaatgat atagaaaaag ggaaattata    1920
gttcgtatta ttcatctaag tgaagagatt aaaacccagg gagtaaataa attgtctaag    1980
gactaaggtt gtatactatt taggtgatag atatggggca accgtatggg ttttatgatt    2040
aacaaataaa cttctcacca ctctaccata tcaactttc cataaaagag agctatagta     2100
ttctttgctt aaataaattt gattagtgca tgacttcttg aaaacatata aagcaaaagt    2160
cacatttgat tctatcagaa aagtgagtaa gccatggccc aaacaaaaga tgcattaaaa    2220
tattctggaa tgatggagct aaaagtaaga aaaatgactt tttaaaaaag tttactgtta    2280
ggaattgtga attatgctg aatttttagtt gcattataat ttttgtcagt catacggtct     2340
gacaacctgt cttatttcta tttccccata tgaggaatgc tagttaagta tggatattaa    2400
ctattactac ttagatgcat tgaagttgca taatatggat aatacttcac tggttccctg    2460
aaaatgttta gttagtaata agtctcttac actatttgtt ttgtccaata atttatattt    2520
tctgaagact taactctaga atacactcat gtcaaaatga aagaatttca ttgcaaaata    2580
ttgcttggta catgacgcat acctgtattt gttttgtgtc acaacatgaa aaatgatggt    2640
ttattagaag tttcattggg taggaaacac atttgaatgg tatttactaa gatactaaaa    2700
tccttggact tcactctaat tttagtgcca tttagaactc aaggtctcag taaaagtaga    2760
aataaagcct gttaacaaaa cacaagctga atattaaaaa tgtaactgga ttttcaaaga    2820
```

```
aatgtttact ggtattacct gtagatgtat attctttatt atgatctttt gtgtaaagtc    2880
tggcagacaa atgcaatatc taattgttga gtccaatatc acaagcagta caaaagtata    2940
aaaaagactt ggccttttct aatgtgttaa atactttat gctggtaata acactaagag     3000
tagggcacta gaaattttaa gtgaagataa tgtgttgcag ttactgcact caatggctta    3060
ctattataaa ccaaaactgg gatcactaag ctccagtcag tcaaaatgat caaaattatt    3120
gaagagaata agcaattctg ttctttatta ggacacagta gatacagact acaaagtgga    3180
gtgtgcttaa taagaggtag catttgttaa gtgtcaatta ctctattatc ccttggagct    3240
tctcaaaata accatataag gtgtaagatg ttaaaggtta tggttacact cagtgcacag    3300
gtaagctaat aggctgagag aagctaaatt acttactggg gtctcacagt aagaaagtga    3360
gctgaagttt cagcccagat ttaactggat tctgggctct ttattcatgt tacttcatga    3420
atctgtttct caattgtgca gaaaaaggg ggctatttat aagaaaagca ataaacaaac     3480
aagtaatgat ctcaaataag taatgcaaga aatagtgaga tttcaaaatc agtggcagcg    3540
atttctcagt tctgtcctaa gtggccttgc tcaatcacct gctatctttt agtggagctt    3600
tgaaattatg tttcagacaa cttcgattca gttctagaat gtttgactca gcaaattcac    3660
aggctcatct ttctaacttg atggtgaata tggaaattca gctaaatgga tgttaataaa    3720
attcaaacgt tttaaggaca gatgaaaatg acagaatttt aaggtaaaat atatgaagga    3780
atataagata aaggattttt ctaccttcag caaaaacata cccactaatt agtaaaatta    3840
ataggcaaaa aaaagttgca tgctcttata ctgtaatgat tatcattta aaactagctt      3900 tttgccttcg agctatcggg gtaaagacct acaggaaaac tactgtcgaa atcctcgagg    3960
ggaagaaggg ggaccctggt gtttcacaag caatccagag gtacgctacg aagtctgtga    4020
cattcctcag tgttcagaag ttgaatgcat gacctgcaat ggggagagtt atcgaggtct    4080
catggatcat acagaatcag gcaagatttg tcagcgctgg gatcatcaga caccacaccg    4140
gcacaaattc ttgcctgaaa gatatcccga caagggcttt gatgataatt attgccgcaa    4200
tcccgatggc cagccgaggc catggtgcta tactcttgac cctcacaccc gctgggagta    4260
ctgtgcaatt aaaacatgcg ctgacaatac tatgaatgac actgatgttc ctttggaaac    4320
aactgaatgc atccaaggtc aaggagaagg ctacaggggc actgtcaata ccatttggaa    4380
tggaattcca tgtcagcgtt gggattctca gtatcctcac gagcatgaca tgactcctga    4440
aaatttcaag tgcaaggacc tacgagaaaa ttactgccga aatccagatg gtctgaatc     4500 accctggtgt tttaccactg atccaaacat ccgagttggc tactgctccc aaattccaaa    4560
ctgtgatatg tcacatggac aagattgtta tcgtgggaat ggcaaaaatt atatgggcaa    4620
cttatcccaa acaagatctg gactaacatg ttcaatgtgg gacaagaaca tggaagactt    4680
acatcgtcat atcttctggg aaccagatgc aagtaagctg aatgagaatt actgccgaaa    4740
tccagatgat gatgctcatg gaccctggtg ctacacggga aatccactca ttccttggga    4800
ttattgccct atttctcgtt gtgaaggtga taccacacct acaatagtca atttagacca    4860
tcccgtaata tcttgtgcca aaacgaaaca attgcgagtt gtaatggga ttccaacacg      4920 aacaaacata ggatggatgg ttagtttgag atacagaaat aaacatatct gcggaggatc    4980
attgataaag gagagttggg ttcttactgc acgacagtgt ttcccttctc gagacttgaa    5040
agattatgaa gcttggcttg gaattcatga tgtccacgga agaggagatg agaaatgcaa    5100
acaggttctc aatgtttccc agctggtata tggccctgaa ggatcagatc tggttttaat    5160
```

| | |
|---|---|
| gaagcttgcc aggcctgctg tcctggatga ttttgttagt acgattgatt tacctaatta | 5220 |
| tggatgcaca attcctgaaa agaccagttg cagtgtttat ggctggggct acactggatt | 5280 |
| gatcaactat gatggcctat tacgagtggc acatctctat ataatgggaa atgagaaatg | 5340 |
| cagccagcat catcgaggga aggtgactct gaatgagtct gaaatatgtg ctggggctga | 5400 |
| aaagattgga tcaggaccat gtgaggggga ttatggtggc ccacttgttt gtgagcaaca | 5460 |
| taaaatgaga atggttcttg gtgtcattgt tcctggtcgt ggatgtgcca ttccaaatcg | 5520 |
| tcctggtatt tttgtccgag tagcatatta tgcaaaatgg atacacaaaa ttattttaac | 5580 |
| atataaggta ccacagtcat ag | 5602 |

<210> SEQ ID NO 8
<211> LENGTH: 4679
<212> TYPE: DNA
<213> ORGANISM: Artificial Sequence
<220> FEATURE:
<223> OTHER INFORMATION: nucleotide sequence of HGF-X6

<400> SEQUENCE: 8

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaggactt | 240 |
| ccattcactt gcaaggcttt tgttttgat aaagcaagaa acaatgcct ctggttcccc | 300 |
| ttcaatagca tgtcaagtgg agtgaaaaa gaatttggcc atgaatttga cctctatgaa | 360 |
| aacaaagact acattagaaa ctgcatcatt ggtaaaggac gcagctacaa gggaacagta | 420 |
| tctatcacta gagtggcat caaatgtcag ccctggagtt ccatgatacc acacgaacac | 480 |
| aggtaagaac agtatgaaga aaagagatga agcctctgtc ttttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa acaatatct taccttaatg cctcaatttg tagatctcgg | 720 |
| tatttgtgga tcccttcctt tctacctgta tttgtcctaa taaattgttg acttattaat | 780 |
| tcactacttc ctcacagctt ttttttggct ttacaaatcc actggaaagg tatatgggtg | 840 |
| tatcactttg tgtatttcgg tgtgcatgtg tagaggggac aaaaatcctc tctcaaacta | 900 |
| taaaattgga gtatttgtgt attgaacatt tgctataact actaggtttc ttaaataatc | 960 |
| ttaatatata aaatgatata gaaaagggaa attatagtt cgtattattc atctaagtga | 1020 |
| agagattaaa acccagggag taataaatt gtctaaggac taaggttgta tactatttag | 1080 |
| gtgatagata tggggcaacc gtatgggttt tatgattaac aaataaactt ctcaccactc | 1140 |
| taccatatca actttttccat aaaagagagc tatagtattc tttgcttaaa taaatttgat | 1200 |
| tagtgcatga cttcttgaaa acatataaag caaaagtcac atttgattct atcagaaaag | 1260 |
| tgagtaagcc atggcccaaa caaaagatgc attaaaatat tctggaatga tggagctaaa | 1320 |
| agtaagaaaa atgactttt aaaaaagttt actgttagga attgtgaaat tatgctgaat | 1380 |
| tttagttgca ttataatttt tgtcagtcat acggtctgac aacctgtctt atttctattt | 1440 |
| ccccatatga ggaatgctag ttaagtatgg atattaacta ttactactta gatgcattga | 1500 |
| agttgcataa tatggataat acttcactgg ttccctgaaa atgtttagtt agtaataagt | 1560 |
| ctcttacact attgtttg tccataatt tatattttct gaagacttaa ctctagaata | 1620 |

```
cactcatgtc aaaatgaaag aatttcattg caaaatattg cttggtacat gacgcatacc   1680
tgtatttgtt ttgtgtcaca acatgaaaaa tgatggttta ttagaagttt cattgggtag   1740
gaaacacatt tgaatggtat ttactaagat actaaaatcc ttggacttca ctctaatttt   1800
agtgccattt agaactcaag gtctcagtaa aagtagaaat aaagcctgtt aacaaaacac   1860
aagctgaata ttaaaaatgt aactggattt tcaagaaaat gtttactggt attacctgta   1920
gatgtatatt cttattatg atcttttgtg taaagtctgg cagacaaatg caatatctaa   1980
ttgttgagtc caatatcaca agcagtacaa agtataaaa aagacttggc cttttctaat   2040
gtgttaaaat actttatgct ggtaataaca ctaagagtag ggcactagaa attttaagtg   2100
aagataatgt gttgcagtta ctgcactcaa tggcttacta ttataaacca aaactgggat   2160
cactaagctc cagtcagtca aaatgatcaa aattattgaa gagaataagc aattctgttc   2220
tttattagga cacagtagat acagactaca aagtggagtg tgcttaataa gaggtagcat   2280
ttgttaagtg tcaattactc tattatccct tggagcttct caaaataacc atataaggtg   2340
taagatgtta aaggttatgg ttacactcag tgcacaggta agctaatagg ctgagagaag   2400
ctaaattact tactgggtc tcacagtaag aaagtgagct gaagtttcag cccagattta   2460
actggattct gggctcttta ttcatgttac ttcatgaatc tgtttctcaa ttgtgcagaa   2520
aaaagggggc tatttataag aaaagcaata acaaacaag taatgatctc aaataagtaa   2580
tgcaagaaat agtgagattt caaaatcagt ggcagcgatt tctcagttct gtcctaagtg   2640
gccttgctca atcacctgct atcttttagt ggagctttga aattatgttt cagacaactt   2700
cgattcagtt ctagaatgtt tgactcagca aattcacagg ctcatctttc taacttgatg   2760
gtgaatatgg aaattcagct aaatggatgt taataaaatt caaacgtttt aaggacagat   2820
gaaaatgaca gaattttaag gtaaaatata tgaaggaata taagataaag gattttteta   2880 ccttcagcaa aaacataccc actaattagt aaaattaata ggcaaaaaaa agttgcatgc   2940
tcttatactg taatgattat cattttaaaa ctagcttttt gccttcgagc tatcggggta   3000
aagacctaca ggaaaactac tgtcgaaatc ctcgagggga agaaggggga ccctggtgtt   3060
tcacaagcaa tccagaggta cgctacgaag tctgtgacat tcctcagtgt tcagaagttg   3120
aatgcatgac ctgcaatggg gagagttatc gaggtctcat ggatcataca gaatcaggca   3180
agatttgtca gcgctgggat catcagacac cacaccggca caaattcttg cctgaaagat   3240 atccccgacaa gggctttgat gataattatt gccgcaatcc cgatggccag ccgaggccat   3300
ggtgctatac tcttgaccct cacacccgct gggagtactg tgcaattaaa acatgcgctg   3360
acaatactat gaatgacact gatgttcctt tggaaacaac tgaatgcatc caaggtcaag   3420
gagaaggcta caggggcact gtcaatacca tttggaatgg aattccatgt cagcgttggg   3480
attctcagta tcctcacgag catgacatga ctcctgaaaa tttcaagtgc aaggacctac   3540
gagaaaatta ctgccgaaat ccagatgggc tgaatcacc ctggtgtttt accactgatc   3600
caaacatccg agttggctac tgctcccaaa ttccaaactg tgatatgtca catggacaag   3660
attgttatcg tgggaatggc aaaaattata tgggcaactt atcccaaaca agatctggac   3720
taacatgttc aatgtgggac aagaacatgg aagacttaca tcgtcatatc ttctgggaac   3780
cagatgcaag taagctgaat gagaattact gccgaaatcc agatgatgat gctcatggac   3840
cctggtgcta cacgggaaat ccactcattc cttgggatta ttgccctatt tctcgttgtg   3900
aaggtgatac cacacctaca atagtcaatt tagaccatcc cgtaatatct tgtgccaaaa   3960
```

-continued

| | |
|---|---|
| cgaaacaatt gcgagttgta aatgggattc caacacgaac aaacatagga tggatggtta | 4020 |
| gtttgagata cagaaataaa catatctgcg gaggatcatt gataaaggag agttgggttc | 4080 |
| ttactgcacg acagtgtttc ccttctcgag acttgaaaga ttatgaagct tggcttggaa | 4140 |
| ttcatgatgt ccacggaaga ggagatgaga atgcaaaca ggttctcaat gtttcccagc | 4200 |
| tggtatatgg ccctgaagga tcagatctgg ttttaatgaa gcttgccagg cctgctgtcc | 4260 |
| tggatgattt tgttagtacg attgatttac ctaattatgg atgcacaatt cctgaaaaga | 4320 |
| ccagttgcag tgtttatggc tggggctaca ctggattgat caactatgat ggcctattac | 4380 |
| gagtggcaca tctctatata tgggaaatg agaaatgcag ccagcatcat cgagggaagg | 4440 |
| tgactctgaa tgagtctgaa atatgtgctg gggctgaaaa gattggatca ggaccatgtg | 4500 |
| agggggatta tggtggccca cttgtttgtg agcaacataa aatgagaatg gttcttggtg | 4560 |
| tcattgttcc tggtcgtgga tgtgccattc caaatcgtcc tggtattttt gtccgagtag | 4620 |
| catattatgc aaaatggata cacaaaatta ttttaacata aaggtacca cagtcatag | 4679 |

<210> SEQ ID NO 9
<211> LENGTH: 3679
<212> TYPE: DNA
<213> ORGANISM: Artificial Sequence
<220> FEATURE:
<223> OTHER INFORMATION: nucleotide sequence of HGF-X7

<400> SEQUENCE: 9

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa aatcagcaaa gactacccta tcaaaatag atccagcact gaagataaaa | 180 |
| accaaaaaag tgaatactgc agaccaatgt gctaatagat gtactaggaa taaaggactt | 240 |
| ccattcactt gcaaggcttt tgtttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |
| tctatcacta gagtggcat caaatgtcag ccctggagtt ccatgatacc acacgaacac | 480 |
| aggtaagaac agtatgaaga aaagagatga agcctctgtc tttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa acaatatct taccttaatg cctcaatttg tagatctcgg | 720 |
| tatttgtgga tcctgggtag gaaacacatt tgaatggtat ttactaagat actaaaatcc | 780 |
| ttggacttca ctctaatttt agtgccattt agaactcaag gtctcagtaa agtagaaat | 840 |
| aaagcctgtt aacaaaacac aaactgaata ttaaaatgt aactggattt tcaaagaaat | 900 |
| gtttactggt attacctgta gatgtatatt cttttattatg atcttttgtg taaagtctgg | 960 |
| cagacaaatg caatatctaa ttgttgagtc caatatcaca agcagtacaa agtataaaa | 1020 |
| aagacttggc cttttctaat gtgttaaaat actttatgct ggtaataaca ctaagagtag | 1080 |
| ggcactagaa attttaagtg aagataatgt gttgcagtta ctgcactcaa tggcttacta | 1140 |
| ttataaacca aaactgggat cactaagctc cagtcagtca aaatgatcaa aattattgaa | 1200 |
| gagaataagc aattctgttc tttattagga cacagtagat acagactaca aagtggagtg | 1260 |
| tgcttaataa gaggtagcat ttgttaagtg tcaattactc tattatccct tggagcttct | 1320 |
| caaaataacc atataaggtg taagatgtta aaggttatgg ttacactcag tgcacaggta | 1380 |

```
agctaatagg ctgagagaag ctaaattact tactggggtc tcacagtaag aaagtgagct    1440
gaagtttcag cccagattta actggattct gggctcttta ttcatgttac ttcatgaatc    1500
tgtttctcaa ttgtgcagaa aaaggggggc tatttataag aaaagcaata aacaaacaag    1560
taatgatctc aaataagtaa tgcaagaaat agtgagattt caaatcagt  ggcagcgatt    1620 tctcagttct gtcctaagtg gccttgctca atcacctgct atcttttagt ggagctttga    1680
aattatgttt cagacaactt cgattcagtt ctagaatgtt tgactcagca aattcacagg    1740
ctcatctttc taacttgatg gtgaatatgg aaattcagct aaatggatgt taataaaatt    1800
caaacgtttt aaggacagat ggaaatgaca gaattttaag gtaaaatata tgaaggaata    1860
taagataaag gatttttcta ccttcagcaa aaacataccc actaattagt aaaattaata    1920
ggcgaaaaaa agttgcatgc tcttatactg taatgattat cattttaaaa ctagcttttt    1980
gccttcgagc tatcgggta aagacctaca ggaaaactac tgtcgaaatc ctcgagggga    2040
agaaggggga ccctggtgtt tcacaagcaa tccagaggta cgctacgaag tctgtgacat    2100
tcctcagtgt tcagaagttg aatgcatgac ctgcaatggg gagagttatc gaggtctcat    2160
ggatcataca gaatcaggca agatttgtca gcgctgggat catcagacac cacaccggca    2220
caaattcttg cctgaaagat atcccgacaa gggctttgat gataattatt gccgcaatcc    2280
cgatggccag ccgaggccat ggtgctatac tcttgaccct cacacccgct gggagtactg    2340
tgcaattaaa acatgcgctg acaatactat gaatgacact gatgttcctt tggaaacaac    2400
tgaatgcatc caaggtcaag gagaaggcta caggggcact gtcaatacca tttggaatgg    2460
aattccatgt cagcgttggg attctcagta tcctcacgag catgacatga ctcctgaaaa    2520
tttcaagtgc aaggacctac gagaaaatta ctgccgaaat ccagatgggt ctgaatcacc    2580
ctggtgtttt accactgatc caaacatccg agttggctac tgctcccaaa ttccaaactg    2640
tgatatgtca catggacaag attgttatcg tgggaatggc aaaaattata tgggcaactt    2700
atcccaaaca agatctggac taacatgttc aatgtgggac aagaacatgg aagacttaca    2760
tcgtcatatc ttctgggaac cagatgcaag taagctgaat gagaattact gccgaaatcc    2820
agatgatgat gctcatggac cctggtgcta cacgggaaat ccactcattc cttgggatta    2880
ttgccctatt tctcgttgtg aaggtgatac cacacctaca atagtcaatt tagaccatcc    2940
cgtaatatct tgtgccaaaa cgaaacaatt gcgagttgta atgggattc  caacacgaac    3000 aaacatagga tggatggtta gtttgagata cagaaataaa catatctgcg gaggatcatt    3060
gataaaggag agtgggttc  ttactgcacg acagtgtttc ccttctcgag acttgaaaga    3120
ttatgaagct tggcttggaa ttcatgatgt ccacggaaga ggagatgaga atgcaaaca     3180 ggttctcaat gtttcccagc tggtatatgg ccctgaagga tcagatctgg ttttaatgaa    3240
gcttgccagg cctgctgtcc tggatgattt tgttagtacg attgatttac ctaattatgg    3300
atgcacaatt cctgaaaaga ccagttgcag tgtttatgc  tggggctaca ctggattgat    3360
caactatgat ggcctattac gagtggcaca tctctatata tgggaaatg  agaaatgcag    3420 ccagcatcat cgagggaagg tgactctgaa tgagtctgaa atatgtgctg gggctgaaaa    3480
gattggatca ggaccatgtg aggggggatta tggtggccca cttgtttgtg agcaacataa    3540
aatgagaatg gttcttggtg tcattgttcc tggtcgtgga tgtgccattc caaatcgtcc    3600
tggtattttt gtccgagtag catattatgc aaaaatggata cacaaaatta ttttaacata    3660
taaggtacca cagtcatag                                                 3679
```

<210> SEQ ID NO 10
<211> LENGTH: 2729
<212> TYPE: DNA
<213> ORGANISM: Artificial Sequence
<220> FEATURE:
<223> OTHER INFORMATION: nucleotide sequence of HGF-X8

<400> SEQUENCE: 10

| | | | | | |
|---|---|---|---|---|---|
| atgtgggtga | ccaaactcct | gccagccctg | ctgctgcagc | atgtcctcct | gcatctcctc | 60 |
| ctgctcccca | tcgccatccc | ctatgcagag | ggacaaagga | aagaagaaa | tacaattcat | 120 |
| gaattcaaaa | atcagcaaa | gactaccta | atcaaaatag | atccagcact | gaagataaaa | 180 |
| accaaaaaag | tgaatactgc | agaccaatgt | gctaatagat | gtactaggaa | taaaggactt | 240 |
| ccattcactt | gcaaggcttt | tgtttttgat | aaagcaagaa | acaatgcct | ctggttcccc | 300 |
| ttcaatagca | tgtcaagtgg | agtgaaaaaa | gaatttggcc | atgaatttga | cctctatgaa | 360 |
| aacaaagact | acattagaaa | ctgcatcatt | ggtaaaggac | gcagctacaa | gggaacagta | 420 |
| tctatcacta | agagtggcat | caaatgtcag | ccctggagtt | ccatgatacc | acacgaacac | 480 |
| aggtaagaac | agtatgaaga | aagagatga | agcctctgtc | ttttttacat | gttaacagtc | 540 |
| tcatattagt | ccttcagaat | aattctacaa | tcctaaaata | acttagccaa | cttgctgaat | 600 |
| tgtattacgg | caaggtttat | atgaattcat | gactgatatt | tagcaaatga | ttaattaata | 660 |
| tgttaataaa | atgtagccaa | aacaatatct | taccttaatg | cctcaatttg | tagatctcgg | 720 |
| tatttgtgga | tccttatgtt | tcagacaact | tcgattcagt | tctagaatgt | ttgactcagc | 780 |
| aaattcacag | gctcatcttt | ctaacttgat | ggtgaatatg | gaaattcagc | taaatggatg | 840 |
| ttaataaaat | tcaaacgttt | taaggacaga | tgaaaatgac | agaattttaa | ggtaaaatat | 900 |
| atgaaggaat | ataagataaa | ggatttttct | accttcagca | aaaacatacc | cactaattag | 960 |
| taaaattaat | aggcaaaaaa | aagttgcatg | ctcttatact | gtaatgatta | tcattttaaa | 1020 |
| actagctttt | tgccttcgag | ctatcggggt | aaagacctac | aggaaaacta | ctgtcgaaat | 1080 |
| cctcgagggg | aagaagggg | accctggtgt | ttcacaagca | atccagaggt | acgctacgaa | 1140 |
| gtctgtgaca | ttcctcagtg | ttcagaagtt | gaatgcatga | cctgcaatgg | ggagagttat | 1200 |
| cgaggtctca | tggatcatac | agaatcaggc | aagatttgtc | agcgctggga | tcatcagaca | 1260 |
| ccacaccggc | acaaattctt | gcctgaaaga | tatcccgaca | agggctttga | tgataattat | 1320 |
| tgccgcaatc | ccgatggcca | gccgaggcca | tggtgctata | ctcttgaccc | tcacacccgc | 1380 |
| tgggagtact | gtgcaattaa | acatgcgct | gacaatacta | tgaatgacac | tgatgttcct | 1440 |
| ttggaaacaa | ctgaatgcat | ccaaggtcaa | ggagaaggct | acaggggcac | tgtcaatacc | 1500 |
| atttggaatg | gaattccatg | tcagcgttgg | gattctcagt | atcctcacga | gcatgacatg | 1560 |
| actcctgaaa | atttcaagtg | caaggaccta | cgagaaaatt | actgccgaaa | tccagatggt | 1620 |
| ctgaatcacc | ctggtgtttt | accactgatc | caaacatccg | agttggctac | tgctcccaaa | 1680 |
| ttccaaactg | tgatatgtca | catggacaag | attgttatcg | tgggaatggc | aaaaattata | 1740 |
| tgggcaactt | atcccaaaca | agatctggac | taacatgttc | aatgtgggac | aagaacatgg | 1800 |
| aagacttaca | tcgtcatatc | ttctgggaac | cagatgcaag | taagctgaat | gagaattact | 1860 |
| gccgaaatcc | agatgatgat | gctcatggac | cctggtgcta | cacgggaaat | ccactcattc | 1920 |
| cttgggatta | ttgccctatt | tctcgttgtg | aaggtgatac | cacacctaca | atagtcaatt | 1980 |
| tagaccatcc | cgtaatatct | tgtgccaaaa | cgaaacaatt | gcgagttgta | aatgggattc | 2040 |
| caacacgaac | aaacataggg | tggatggtta | gtttgagata | cagaaataaa | catatctgcg | 2100 |

```
gaggatcatt gataaaggag agttgggttc ttactgcacg acagtgtttc ccttctcgag    2160
acttgaaaga ttatgaagct tggcttggaa ttcatgatgt ccacggaaga ggagatgaga    2220
aatgcaaaca ggttctcaat gtttcccagc tggtatatgg ccctgaagga tcagatctgg    2280
ttttaatgaa gcttgccagg cctgctgtcc tggatgattt tgttagtacg attgatttac    2340
ctaattatgg atgcacaatt cctgaaaaga ccagttgcag tgtttatggc tggggctaca    2400
ctggattgat caactatgat ggcctattac gagtggcaca tctctatata tgggaaatg     2460 agaaatgcag ccagcatcat cgagggaagg tgactctgaa tgagtctgaa atatgtgctg    2520
gggctgaaaa gattggatca ggaccatgtg aggggattga tggtggccca cttgtttgtg    2580
agcaacataa aatgagaatg gttcttggtg tcattgttcc tggtcgtgga tgtgccattc    2640
caaatcgtcc tggtattttt gtccgagtag catattatgc aaaatggata cacaaaatta    2700
ttttaacata taaggtacca cagtcatag                                      2729

<210> SEQ ID NO 11
<211> LENGTH: 20
<212> TYPE: DNA
<213> ORGANISM: Artificial Sequence
<220> FEATURE:
<223> OTHER INFORMATION: Forward primer for BAX gene

<400> SEQUENCE: 11
ggcagacagt gaccatcttt                                                 20

<210> SEQ ID NO 12
<211> LENGTH: 20
<212> TYPE: DNA
<213> ORGANISM: Artificial Sequence
<220> FEATURE:
<223> OTHER INFORMATION: Reverse primer for BAX gene

<400> SEQUENCE: 12
agtggacctg aggtttattg                                                 20

<210> SEQ ID NO 13
<211> LENGTH: 20
<212> TYPE: DNA
<213> ORGANISM: Artificial Sequence
<220> FEATURE:
<223> OTHER INFORMATION: Forward primer for BCL-2 gene

<400> SEQUENCE: 13
ccatcaatca aagccaagca                                                 20

<210> SEQ ID NO 14
<211> LENGTH: 20
<212> TYPE: DNA
<213> ORGANISM: Artificial Sequence
<220> FEATURE:
<223> OTHER INFORMATION: Reverse primer for BCL-2 gene

<400> SEQUENCE: 14
agccttcacg caagttcagg                                                 20

<210> SEQ ID NO 15
<211> LENGTH: 22
<212> TYPE: DNA
<213> ORGANISM: Artificial Sequence
<220> FEATURE:
<223> OTHER INFORMATION: Forward primer for GAPDH gene
```

```
<400> SEQUENCE: 15
ccatcactgc cactcagaag ac                                              22

<210> SEQ ID NO 16
<211> LENGTH: 21
<212> TYPE: DNA
<213> ORGANISM: Artificial Sequence
<220> FEATURE:
<223> OTHER INFORMATION: Reverse primer for GAPDH gene

<400> SEQUENCE: 16
tcatacttgg caggtttctc c                                               21
```

METHOD FOR TREATING AMYOTROPHIC LATERAL SCLEROSIS WITH A POLYNUCLEOTIDE ENCODING TWO OR MORE ISOFORMS OF HEPATOCYTE GROWTH FACTOR

TECHNICAL FIELD

The present application is the National Stage of International Application No. PCT/KR2014/009971, filed Oct. 22, 2014, which claims priorities from Korean Patent Application No. 10-2013-0126216 filed with the Korean Intellectual Property Office on 22 Oct. 2013 and Korean Patent Application No. 10-2014-0143377 filed with the Korean Intellectual Property Office on 22 Oct. 2014, the disclosures of which are incorporated herein by reference.

The present invention relates to a composition, containing, as an active ingredient, two or more isoforms of hepatocyte growth factor or a polynucleotide encoding the isoforms, for preventing or treating amyotrophic lateral sclerosis.

BACKGROUND ART

Amyotrophic lateral sclerosis (ALS), which is a motor neuron disease, was first reported in 1869 by French doctor Jean-Martin Chartcot. ALS was known to normal people since Lou Gehrig, a famous baseball player in the United State who suffered from this disease, in 1939, and from this moment, ALS was called Lou Gehrig's disease.

The prognosis of ALS is based on clinical features, electric diagnosis tests, and the exclusion of other health states associated with the symptoms. The molecular genetic test, which can be used in clinical tests associated with some genes involved in ALS, plays an important role in genetic type determination and genetic counseling.

ALS may be inherited in an autosomal dominant, autosomal recessive, or X-linked manner. Genetic counseling and risk assessment depend on the accurate diagnosis of particular genes.

Riluzole has been known as a drug used to delay the progress of ALS. It is known that Riluzole can lower the rate of ALS progress by inhibiting excessive glutamic acid, which is considered to be one of the causes of motor neuron destruction. However, the clinical effects of Riluzole fail to alleviate ALS symptoms, and the results thereof are also not obvious in extending the tracheotomy-free survival of ALS patients receiving no tracheotomy. As described above, the genuine clinical effects of Riluzole, which is helpful to ALS patients, have been reported to be very restricted and obscure (Stewart et al, 2001). Nevertheless, there is no effective preventive or therapeutic agent for ALS, excluding Riluzole having even equivocal clinical effectiveness, and thus the development of drugs exhibiting the effects of preventing or treating ALS is needed.

Meanwhile, expression vectors as a gene delivery system for genetic therapy have been known in the conventional art. The detailed descriptions of pCK vector used in an example of the present invention are disclosed in PCT/KR1999/000855. In addition, PCT/KR2003/000548 discloses a composition, containing pCK-HGFX7 recombinant vector used in the present invention, for treating or preventing ishemic diseases or liver disorders. The entire contents of PCT/KR1999/000855 and PCT/KR2003/000548 are incorporated herein by reference.

Throughout the entire specification, many papers and patent documents are referenced and their citations are represented. The disclosure of the cited papers and patent documents are entirely incorporated by reference into the present specification and the level of the technical field within which the present invention falls, and the details of the present invention are explained more clearly.

DETAILED DESCRIPTION OF THE INVENTION

Technical Problem

The present inventors researched and endeavored to develop drugs capable of preventing or treating amyotrophic lateral sclerosis (ALS). As a result, the present inventors established that ALS can be treated by using a composition containing, as an active ingredient, two or more isoforms of hepatocyte growth factor (HGF) or a polynucleotide encoding the isoforms, and thus have completed the present invention.

Therefore, an aspect of the present invention is to provide a pharmaceutical composition for preventing or treating amyotrophic lateral sclerosis.

Another aspect of the present invention is to provide a method for preventing or treating amyotrophic lateral sclerosis.

Other purposes and advantages of the present disclosure will become more obvious with the following detailed description of the invention, claims, and drawings.

Technical Solution

In accordance with an aspect of the present invention, there is provided a pharmaceutical composition for preventing or treating amyotrophic lateral sclerosis, the composition containing, as an active ingredient, two or more isomers of hepatocyte growth factor (HGF) or a polynucleotide encoding the isomers.

The present inventors researched and endeavored to develop drugs capable of preventing or treating amyotrophic lateral sclerosis. As a result, the present inventors established that ALS could be treated by using a composition containing, as an active ingredient, two or more isoforms of hepatocyte growth factor (HGF) or a polynucleotide encoding the isoforms.

The therapy strategy of the present invention may be largely classified into two types: protein therapy and gene therapy. According to the protein therapeutic agent strategy of the present invention, two or more types of isomeric proteins of HGF are used. Meanwhile, according to the gene therapeutic agent strategy of the present invention, at least one nucleotide sequence encoding two or more types of isomers of HGF is used. A two or more HGF isoforms-encoding polynucleotide sequence may be provided by one polynucleotide or separate polynucleotides. Preferably, the two or more HGF isoforms-encoding polynucleotide sequence is provided by one polynucleotide.

Hereinafter, the present invention will be described in detail.

As used herein, the term "HGF isoform (or isomer of HGF)" refers to an HGF polypeptide having an amino acid sequence that is at least 80% identical to the naturally occurring HGF amino acid sequence in an animal, including all allelic variants. For example, the HGF isoform has a meaning that includes all of a normal form or a wild type of HGF and various variants of HGF (e.g., splicing variants and deleted variants).

In an embodiment of the present invention, the two or more isoforms of HGF include full-length HGF (flHGF) and deleted variant HGF (dHGF). The use of a composition containing both the full-length HGF and the deleted variant HGF can prevent or treat ALS very effectively.

As used herein, the term "flHGF" refers to a sequence of amino acids 1-728 of the HGF protein from an animal, preferably a mammal, and more preferably a human.

As used herein, the term "dHGF" refers to a deleted variant of the HGF protein produced by alternative splicing of the HGF gene from an animal, preferably a mammal, and more preferably refers to human HGF consisting of 723 amino acids, with the deletion of five amino acids (F, L, P, S, and S) in the first kringle domain of the alpha chain from the full-length HGF sequence.

In an embodiment of the present invention, the full-length HGF of the present invention includes the amino acid sequence of SEQ ID NO: 1, and the deleted variant HGF of the present invention includes the amino acid sequence of SEQ ID NO: 2.

In an embodiment of the present invention, the HGF isoforms of the present invention are encoded by separate nucleotide sequences or a single polynucleotide sequence. Herein, the pharmaceutical composition of the present invention includes two or more polynucleotides when the different types of isoforms of HGF are encoded by separate polynucleotides, and includes at least one polynucleotide including the single polynucleotide when the different types of isoforms of HGF are encoded by the single polynucleotide sequence. The polynucleotide of the present invention may be operatively linked to at least one regulatory sequence (e.g., a promoter or an enhancer) regulating the expression of the HGF isoforms.

When the two or more types of isoforms of HGF are encoded by separate polynucleotides, an expression cassette may be constructed in two manners. According to a first manner, the expression cassette is constructed by linking an expression regulatory sequence to a coding sequence (CDS) of each isoform. According to a second manner, the expression cassette is constructed by using an internal ribosomal entry site (IRES) and 2A peptides, like "expression regulatory sequence—first isomer CDS—IRES—second isomer CDS—transcription termination sequence". The IRES allows the gene translation to start at the IRES sequence, thereby expressing two or more genes of interest in the same construct.

When two or more types of isoforms of HGF are encoded by a single polynucleotide, the polynucleotide encoding all the two or more types of isoforms is operatively linked to a single expression regulatory sequence.

In the present invention, the HGF isoforms may be encoded by a hybrid HGF gene that simultaneously expresses two or more different types of isoforms of HGF, e.g., flHGF and dHGF.

According to a preferable embodiment of the present invention, the hybrid HGF gene includes cDNA corresponding exons 1 to 18 of human HGF and intron 4 of the human HGF gene or a fragment thereof, which is inserted between exon 4 and exon 5 of the cDNA.

According to a more preferable embodiment of the present invention, the hybrid HGF gene includes a nucleotide sequence selected from the group consisting of SEQ ID NO: 3 to SEQ ID NO: 10.

The hybrid HGF gene including intron 4 is 7113 by long and includes the nucleotide sequence of SEQ ID NO: 3. The hybrid HGF gene may selectively include a fragment of intron 4 between exon 4 and exon 5 of HGF cDNA.

According to a preferable embodiment of the present invention, the sequence additionally inserted between exon 4 and exon 5 includes: intron 4 of the human HGF gene, nucleotides 392-2247, nucleotides 392-727, nucleotides 2229-5471, nucleotides 5117-5471, nucleotides 3167-5471, nucleotides 4167-5471, or a combination thereof, of the nucleotide sequence of SEQ ID NO: 3.

More preferably, the sequence additionally inserted between exon 4 and exon 5 of the therapeutic nucleotide sequence used in the present invention is (i) nucleotides 392-2247 and nucleotides 2229-5471 of SEQ ID NO: 3; (ii) nucleotides 392-2247 and nucleotides 5117-5471 of SEQ ID NO: 3; (iii) nucleotides 392-2247 and nucleotides 3167-5471 of SEQ ID NO: 3; (iv) nucleotides 392-2247 and nucleotides 4167-5471 of SEQ ID NO: 3; (v) nucleotides 392-727 and nucleotides 2229-5471 of SEQ ID NO: 3; (vi) nucleotides 392-727 and nucleotides 5117-5471 of SEQ ID NO: 3; (vii) nucleotides 392-727 and nucleotides 3167-5471 of SEQ ID NO: 3; or (viii) nucleotides 392-727 and nucleotides 4167-5471 of SEQ ID NO: 3.

The therapeutic nucleotide sequence of the present invention according to the sequence additionally inserted between exon 4 and exon 5 is summarized as below: (i) (exon 1 to exon 4)-(nucleotides 392-2247-nucleotides 2297-5471 of SEQ ID NO: 3)-(exon 5 to exon 18); (ii) (exon 1 to exon 4)-(nucleotides 392-2247-nucleotides 5117-5471 of SEQ ID NO: 3)-(exon 5 to exon 18); (iii) (exon 1 to exon 4)-(nucleotides 392-2247-nucleotides 392-5471 of SEQ ID NO: 3)-(exon 5 to exon 18); (iv) (exon 1 to exon 4)-(nucleotides 392-2247-nucleotides 4167-5471 of SEQ ID NO: 3)-(exon 5 to exon 18); (v) (exon 1 to exon 4)-(nucleotides 392-727-nucleotides 2229-5471 of SEQ ID NO: 3)-(exon 5 to exon 18); (vi) (exon 1 to exon 4)-(nucleotides 392-727-nucleotides 5117-5471 of SEQ ID NO: 3)-(exon 5 to exon 18); (vii) (exon 1 to exon 4)-(nucleotides 392-727-nucleotides 3167-5471 of SEQ ID NO: 3)-(exon 5 to exon 18); and (viii) (exon 1 to exon 4)-(nucleotides 392-727-nucleotides 4167-5471 of SEQ ID NO: 3)-(exon 5 to exon 18).

Herein, the hybrid HGF gene including the fragment of intron 4 is named "HGF-X", and the HGF-X includes HGF-X2, HGF-X3, HGF-X4, HGF-X5, HGF-X6, HGF-X7, and HGF-X8, which have nucleotide sequences of SEQ ID NOs: 4 to 10. In the present invention, HGF-X7 is preferably used. The "HGF isoform", "HGF-X", and "HGF-X7" in the present invention have been reported in PCT/KR2003/000548, the disclosure of which is incorporated herein by reference.

Amino acid or nucleotide sequences of the HGF isoforms, which may be used in the present invention, are construed to include amino acid or nucleotide sequences having substantial identity to the sequences of wild type human HGF isoforms. that, when the amino The term "substantial identity" means acid or nucleotide sequence of the wild type human HGF isoform and another nucleotide sequence are aligned to correspond to each other as much as possible and the aligned sequences are analyzed using an algorithm 25 that is normally used in the art, the amino acid or nucleotide sequence of the wild type human HGF isoform shows at least 80% identity, preferably at least 90% identity, and most preferably at least 95% identity. Methods of alignment for the sequence comparison are well 30 known in the art. Various methods and algorithms for alignment are disclosed in Smith and Waterman, Adv. Appl. Math. 2:482 (1981); Needleman and Wunsch, J. Mol. Bio. 4 8: 4 4 3 (1970); Pearson and Lipman, Methods in Mol. Biol. 24:307-31 (1988); Higgins and Sharp, Gene 73:237-44 (1988); Higgins and Sharp, CABIOS 5: 151-3 (1989); Corpet et al., Nuc. Acids Res. 16:10881-90 (1988); Huang et al., Comp. 5 Appl. BioSci. 8: 155-65 (1992); and Pearson et al., Meth. Mol. Biol. 24:307-31 (1994). The NCBI Basic Local Alignment Search Tool (BLAST) (Altschul et al., J. Mol. Biol. 215: 403-10 (1990)) is available via the National Center for Biological Information (NCBI) and, on the Internet, may be used in connection with the sequence analysis programs, such as blastp, blasm, blastx, tblastn, and tblastx. BLAST can be accessed through the BLAST page of the ncbi website. The sequence identity comparison method using such a program can be confirmed in the BLAST help page of the ncbi website.

As used herein, the term "prevention" refers to all the actions of suppressing amyotrophic lateral sclerosis or delaying the progress of amyotrophic lateral sclerosis through administration of the composition of the present invention.

The term "treatment" used herein refers to (a) the suppression of the progress of amyotrophic lateral sclerosis, (b) the relief of amyotrophic lateral sclerosis, or (c) the removal of amyotrophic lateral sclerosis.

The composition of the present invention can prevent or treat amyotrophic lateral sclerosis through the neurite outgrowth and growth as well as the growth and anti-apoptosis of motor neurons.

The composition of the present invention may be applied in vivo through various delivery methods that are conventionally known in the gene therapy field.

In an embodiment of the present invention, the polynucleotide of the present invention is naked DNA or is contained in a gene delivery system. Examples of the gene delivery system include a plasmid, a vector, and a viral vector.

(i) Plasmid (Vector)

A plasmid (vector) may be used as a delivery system that delivers the polynucleotide of the present invention. The polynucleotide included in the vector preferably exists in an appropriate expression cassette. Preferably, the polynucleotide is operatively linked to a promoter in the expression cassette.

As used herein, the term "operatively linked" refers to a functional linkage between a nucleic acid expression regulatory sequence (e.g., a promoter, signal sequence, or an array at the binding site of a transcription regulation factor) and another nucleic acid sequence, and through the linkage, the regulatory sequence regulates the transcription and/or translation of another nucleic acid sequence.

In the present invention, the promoter binding to the polynucleotide sequence is one that can regulate the transcription of the nucleotide sequence by operating in animal cells, preferably mammalian cells, and more preferably human cells, and includes, for example, promoters derived from mammalian viruses and promoters derived from mammalian cell genomes. Examples thereof may include cytomegalovirus (CMV) promoter, adenovirus late promoter, vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, and human GM-CSF gene promoter, but are not limited thereto. Still more preferably, the promoter used in the present invention is a promoter derived from the human CMV (hCMV) immediately early (IE) gene, or an EF1 alpha promoter, and most preferably, a 5'-untranslated region (UTR) including promoter/enhancer and the entire sequence of exon 1 immediately to ATG initiation codon of exon 2, of the hCMV IE gene.

The expression cassette used in the present invention may include a polyadenylation sequence, for example, a bovine growth hormone terminator (Gimmi, E. R., et al., Nucleic Acids Res. 17:6983-6998 (1989)), SV40-derived polyadenylation sequence (Schek, N, et al., Mol. Cell Biol. 12:5386-5393 (1992)), HIV-1 polyA (Klasens, B. I. F., et al., Nucleic Acids Res. 26:1870-1876 (1998)), β-globin polyA (Gil, A., et al, Cell 49:399-406 (1987)), HSV TK polyA (Cole, C. N. and T. P. Stacy, Mol. Cell. Biol. 5:2104-2113 (1985)) or polyoma virus poly A (Batt, D. B and G. G. Carmichael, Mol. Cell. Biol. 15:4783-4790 (1995)), but are not limited thereto.

According to a preferable embodiment of the present invention, pCK, pCP, pVAX1, or pCY vector may be used as a delivery system of the polynucleotide, and more preferably, pCK vector may be used. The pCK vector is disclosed in detail in WO 2000/040737, the disclosure of which is incorporated herein by reference.

(ii) Retrovirus

Retrovirus can introduce a gene thereof into the genome of a host to deliver a lot of exotic genetic materials, and has a wide spectrum of infectible cells, so most retroviruses are used as a gene delivery vector.

In order to construct the retroviral vector, the polynucleotide sequence of the present invention is inserted into the retroviral genome but not the retroviral sequence, thereby producing replication-defective viruses. For virion production, a packaging cell line containing gag, pol, and env genes but having no long terminal repeat (LTR) sequence and ψ sequence is constructed (Mann et al., Cell, 33:153-159 (1983)). When the recombinant plasmid containing the polynucleotide sequence of the present invention, the LTR sequence, and the ψ sequence is introduced into the cell line, the ψ sequence allows the production of RNA transcripts of the recombinant plasmid, and these transcripts are packaged with viruses, which are discharged to the media (Nicolas and Rubinstein "Retroviral vectors," In: Vectors: A survey of molecular cloning vectors and their uses, Rodriguez and Denhardt (eds.), Stoneham: Butterworth, 494-513 (1988)). The media containing the recombinant retroviruses are collected and concentrated, and then used as a gene delivery system.

The gene delivery using second-generation retroviral vectors has been published. Kasahara et al., manufactured a moloney murine leukemia virus variant, and produced a chimeric protein having new binding characteristics by inserting the erythropoietin (EPO) sequence into the envelope site thereof (Science, 266:1373-1376 (1994)). The polynucleotide sequence of the present invention may also be introduced into the retrovirus according to the construction strategy of the second-generation retrovirus vector.

(iii) Adenovirus

Adenovirus has usually been employed as a gene delivery vector due to the mid-sized genome, ease of engineering, high titer, wide range of target cells, and high infectivity. Both ends of the genome contain 100-200 by inverted terminal repeats (ITRs), which are cis-elements necessary for DNA replication and packaging. E1 region (E1A and E1B) of the genome encodes proteins responsible for the regulation of transcription of the viral genome and the transcription of host cell genes. E2 region (E2A and E2B) encodes the proteins involved in viral DNA replication.

Out of the adenoviral vectors developed so far, the replication-defective adenovirus having the deleted E1 region is usually used. Meanwhile, the deleted E3 region in normal adenoviral vectors may provide an insertion site for exotic genes (Thimmappaya, B. et al., Cell, 31:543-551 (1982); and Riordan, J. R. et al., Science, 245:1066-1073 (1989)). Therefore, the polynucleotide sequence of the present invention is preferably inserted into either the deleted E1 region (E1A region and/or E1B region) or the deleted E3 region. In addition, the polynucleotide sequence may also be inserted into the deleted E4 region. Herein, the term "deletion" used with reference to viral genome sequences encompasses the complete deletion of the corresponding sequence as well as the partial deletion thereof. In addition, the adenovirus can package approximately 105% of the wild-type genome, providing capacity for about 2 extra kb of DNA (Ghosh-Choudhury et al., *EMBO J.,* 6:1733-1739 (1987)). Therefore, the foregoing exotic sequences inserted into the adenovirus may be further coupled with the adenoviral genome.

Adenovirus may be of any of 42 different serotypes and subgroups A-F. Of these, adenovirus type 5 pertaining to subgroup C is the most preferable starting material for obtaining the adenoviral vector of the present invention. Biochemical and genetic information about adenovirus type 5 has been well known. The exotic genes delivered by the adenovirus are replicated in the same manner as in the episome, and thus have low genotoxicity to host cells. Therefore, the gene therapy using the adenoviral gene delivery system is determined to be safe.

(iv) AAV Vector

Adeno-associated viruses (AAV) are capable of infecting non-divided cells and have the ability to infect various types of cells, and thus are suitable as a gene delivery system of this invention. Detailed descriptions for the use and preparation of the AAV vector are disclosed in U.S. Pat. Nos. 5,139,941 and 4,797,368.

Research results for AAV as a gene delivery system are disclosed in LaFace et al, Viology, 162:483486 (1988), Zhou et al., Exp. Hematol. (NY), 21:928-933 (1993), Walsh et al, J. Clin. Invest., 94:1440-1448 (1994), and Flotte et al., Gene Therapy, 2:29-37 (1995). Recently, the AAV vector has been approved for Phase I human trials for the treatment of cystic fibrosis.

Typically, the AAV virus is manufactured by co-transfecting a plasmid containing a target gene sequence flanked by two AAV terminal repeats (McLaughlin et al., J. Virol., 62:1963-1973 (1988); and Samulski et al., J. Virol., 63:3822-3828 (1989)) and an expression plasmid containing a wild type AAV coding sequence without terminal repeats (McCarty et al., J. Virol., 65:2936-2945 (1991)).

(v) Other Viral Vectors

Other viral vectors may be used to deliver the polynucleotide sequence of the present invention into the biology body. Vectors derived from viruses, such as vaccinia virus (Puhlmann M. et al., Human Gene Therapy 10:649-657 (1999); Ridgeway, "Mammalian expression vectors," In: Vectors: A survey of molecular cloning vectors and their uses. Rodriguez and Denhardt, eds. Stoneham: Butterworth, 467-492 (1988); Baichwal and Sugden, "Vectors for gene transfer derived from animal DNA viruses: Transient and stable expression of transferred genes," In: Kucherlapati R, ed. Gene transfer. New York: Plenum Press, 117-148 (1986) and Coupar et al., Gene, 68:1-10 (1988)), lentivirus (Wang G. et al., J. Clin. Invest. 104(11):R55-62 (1999)), or herpes simplex virus (Chamber R., et al., Proc. Natl. Acad. Sci USA 92:1411-1415 (1995)) may also be used as a delivery system capable of delivering the polynucleotide into cells.

(vi) Liposomes

Liposomes are formed spontaneously by phospholipids suspended in the aqueous medium. Liposome-mediated exotic DNA molecule delivery has been very successful as described in Nicolau and Sene, Biochim. Biophys. Acta, 721:185-190 (1982) and Nicolau et al., Methods Enzymol., 149:157-176 (1987). Liposomes entrapping the polynucleotide sequence of the present invention delivery the polynucleotide sequence into cells by interacting with cells through mechanisms, such as endocytosis, adsorption onto cell surfaces, and fusion with plasma cellular membranes.

In cases where the polynucleotide sequence of the present invention is introduced in a naked recombinant DNA molecule or a plasmid (vector), the polynucleotide sequence may be introduced into cells by micro-injection (Capecchi, M. R., Cell, 22:479 (1980); and Harland & Weintraub, J. Cell Biol. 101:1094-1099 (1985)), phosphate calcium precipitation (Graham, F. L. et al., Virology, 52:456 (1973); and Chen & Okayama, Mol. Cell. Biol. 7:2745-2752 (1987)), electroporation (Neumann, E. et al., EMBO J., 1:841 (1982); and Tur-Kaspa et al., Mol. Cell Biol., 6:716-718 (1986)), liposome-mediated transfection (Wong, T. K. et al., Gene, 10:87 (1980); Nicolau & Sene, Biochim. Biophys. Acta, 721:185-190 (1982); and Nicolau et al., Methods Enzymol., 149:157-176 (1987)), DEAE-dextran treatment (Gopal, Mol. Cell Biol., 5:1188-1190 (1985)) and gene bombardment (Yang et al., Proc. Natl. Acad. Sci., 87:9568-9572 (1990)).

When the polynucleotide sequence of the present invention is constructed based on the viral vector, the polynucleotide sequence may be delivered into cells by various viral infection methods known in the art. The infection of host cells using viral vectors are described in the above-mentioned cited documents.

In a preferable embodiment of the present invention, the gene delivery system of the present invention is a vector.

In an embodiment of the present invention, the vector of the present invention is a plasmid, and most preferably, the pCK vector may be used. An example of the recombinant vector including a single polynucleotide expressing two or more isomers of HGF using the pCK vector may be pCK-HGFX7, the contents of which are described in detail in PCT/KR1999/000855 and PCT/KR2003/000548, as described above.

The composition of the present invention may contain a pharmaceutically acceptable carrier. The pharmaceutically acceptable carrier contained in the composition of the present invention is conventionally used for the formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain a lubricant, a wetting agent, a sweetening agent, a flavoring agent, an emulsifier, a suspending agent, a preservative, and the like, in addition to the above ingredient. Suitable pharmaceutically acceptable carriers and agents are described in detail in *Remington's Pharmaceutical Sciences* (19th ed., 1995).

Preferably, the pharmaceutical composition of this invention may be administered parenterally, and for example, intravenous administration, intraperitoneal administration, subcutaneous administration, intradermal administration, intraspinal administration, intrathecal administration, intraventricular administration, parenchymal administration, intracranial administration, intramuscular administration, or local administration may be employed. Most preferably, the pharmaceutical composition of this invention may be administered intramuscularly, spinally, intrathecally, intraventricularly, parenchymally, or intracranially.

The pharmaceutical composition of the present invention may be formulated and administered as an injection. The appropriate dose of the pharmaceutical composition of the present invention varies depending on factors, such as the formulating method, manner of administration, patient's age, body weight, gender, and severity of disease, time of administration, route of administration, excretion rate, and response sensitivity, and the ordinarily skilled practitioner can easily judge and prescribe the dose effective for desired treatment or prevention.

According to a preferable embodiment of the present invention, the isoforms of HGF of the present invention are administered at a dose of 1 µg to 2,500 mg for each, and the polynucleotide encoding the isoforms is administered at a dose of 1 µg to 2,500 mg. When the isoforms of HGF or the polynucleotide encoding the isoforms is repeatedly administered once or more, the dose may be equal or different for each administration.

The pharmaceutical composition of the present invention is formulated using a pharmaceutically acceptable carrier and/or excipient, according to the method that is easily conducted by person having ordinary skills in the art to which the present invention pertains, and the pharmaceutical composition may be prepared into a unit dosage form or may be inserted into a multidose container. Here, the dosage form may be a solution in an oily or aqueous medium, a suspension, an emulsion, an extract, a powder, granules, a tablet, or a capsule, and may further contain a dispersant or a stabilizer.

In accordance with another aspect of the present invention, there is provided a method for preventing or treating amyotrophic lateral sclerosis, the method including administering, to a mammal, a composition containing, as an active ingredient, two or more isomers of hepatocyte growth factor (HGF) or a polynucleotide encoding the isomers.

In an embodiment of the present invention, the two or more HGF isoforms of the present invention include full-length HGF (flHGF) and deleted variant HGF (dHGF).

In an embodiment of the present invention, the full-length HGF of the present invention includes the amino acid sequence of SEQ ID NO: 1, and the deleted variant HGF of the present invention includes the amino acid sequence of SEQ ID NO: 2.

Since the method for preventing or treating amyotrophic lateral sclerosis of the present invention includes the step of administering the pharmaceutical composition for preventing or treating amyotrophic lateral sclerosis, which is an aspect of the present invention, the overlapping descriptions therebetween are omitted to avoid excessive complication of the specification due to repetitive descriptions thereof.

Advantageous Effects

Features and advantages of the present invention are summarized as follows:

(a) The present invention provides a pharmaceutical composition for preventing or treating amyotrophic lateral sclerosis.

(b) The present invention provides a method for preventing or treating amyotrophic lateral sclerosis.

(c) The composition or method of the present invention may be used to prevent or treat amyotrophic lateral sclerosis through the neurite outgrowth and growth in embryonic neural cells as well as the growth and anti-apoptosis of motor neurons.

BRIEF DESCRIPTION OF THE DRAWINGS

FIG. 3 depicts an effect of pCK-HGFX7 on cell growth in NSC-34 cells according to an embodiment of the present invention.

FIG. 4A shows Bax (dark) or Bcl-2 (light) mRNA expression levels in NSC-34 cells treated with supernatants obtained from 293 T cells transfected with pCK, pCK-HGF728, pCK-HGF723, or pCK-HGFX7. The expression levels are presented as ratios between expression levels in NSC-34 in each condition and those in NSC-34 cells treated with supernatants from 293 T cells transfected with pCK. FIG. 4B provides ratios between Bax and Bcl-2 mRNA expression levels in NSC-34 cells treated with supernatants obtained from 293 T cells transfected with pCK, pCK-HGF728, pCK-HGF723, or pCK-HGFX7.

FIG. 5 depicts an effect of pCK-HGFX7 on the survival of NSC-34 cells under oxidative stress culture conditions according to an embodiment of the present invention.

FIG. 6A shows Bax (dark) or Bcl-2 (light) mRNA expression levels in NSC-34 cells under oxidative stress culture conditions, treated with supernatants obtained from 293 T cells transfected with pCK, pCK-HGF728, pCK-HGF723, or pCK-HGFX7. The expression levels are presented as ratios between mRNA expression levels in NSC-34 cells in each condition and those in NSC-34 cells treated with supernatants from 293 T cells transfected with pCK. FIG. 6B provides ratios between Bax and Bcl-2 mRNA expression levels in NSC-34 cells under oxidative stress culture conditions, treated with supernatants obtained from 293 T cells transfected with pCK, pCK-HGF728, pCK-HGF723, or pCK-HGFX7.

FIG. 7 depicts an effect of pCK-HGFX7 on cell growth in the G93A mutant hSOD1-delivered cells according to an embodiment of the present invention.

FIG. 8 depicts an effect of pCK-HGFX7 on grip strength in ALS mice according to an embodiment of the present invention.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Verification on Effect of pCK-HGFX7 on Maturation of Embryonic Neuronal Cell (ENC)

Only the cerebral cortex portion was taken from the mouse embryo to be made into single cells, and then 10 µM Ara-C 10 was added to the culture medium to culture only neuronal cells. In order to verify the effect of pCK-HGFX7 on the maturation of ENC, $2 \times 10^4$ cells were seeded, and the next day, the cells were treated with 1.25 ng/ml of the protein obtained from 293F cells (Life technologies, USA) transfected with pCK-HGFX7, thereby verifying the degree of neurite outgrowth shown in the cell maturation. The degree of neurite outgrowth was confirmed through immunocytochemistry on the expression of TUJ-1, which is a tubulin protein expressed specifically to neuronal cells.

Figure 1:
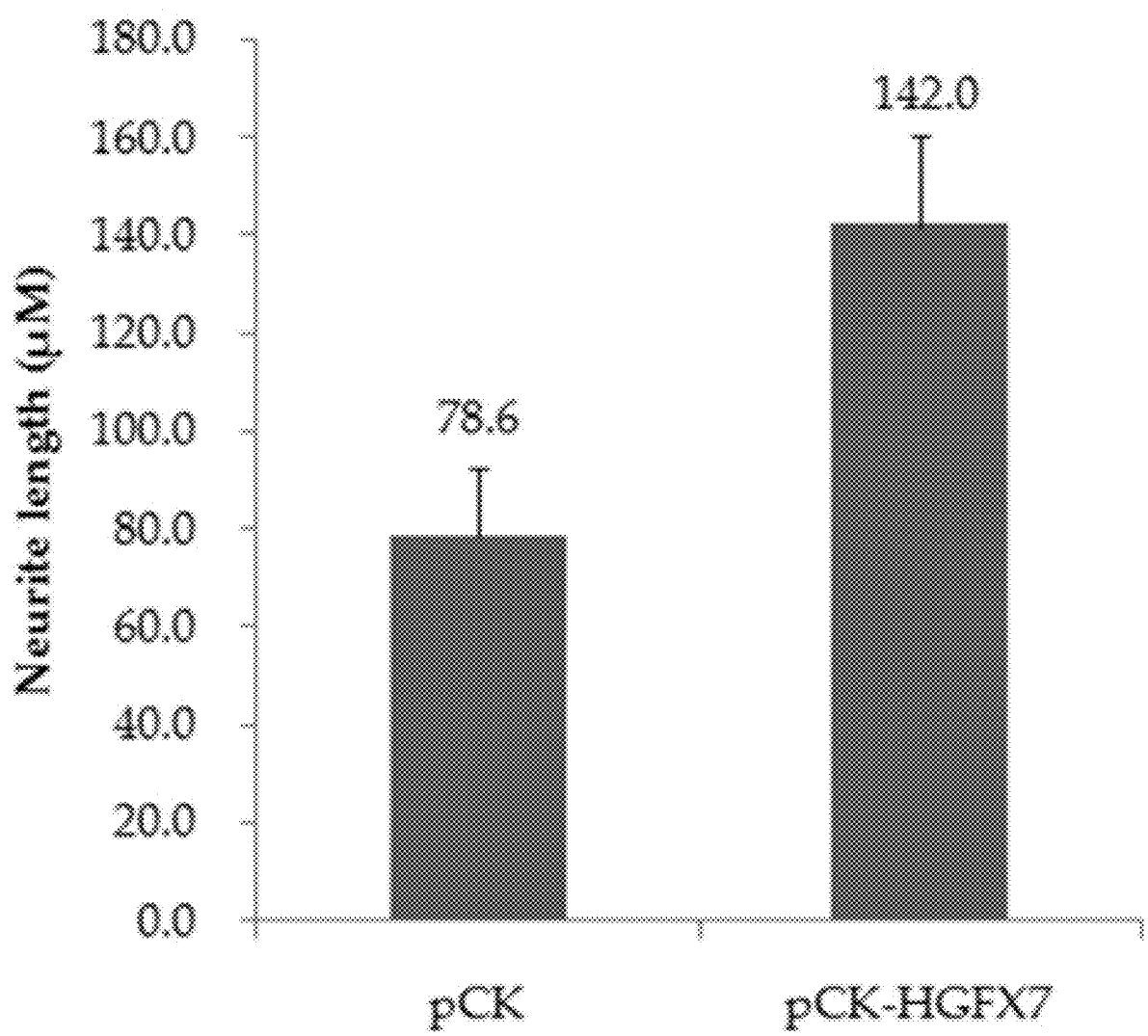
FIG. 1 depicts an effect of pCK-HGFX7 on the neurite outgrowth of ENC cells according to an embodiment of the present invention.

The results confirmed that, as shown in FIG. 1, the neurite length was significantly increased in the pCK-HGFX7 treatment group rather than the pCK treatment group as a control.

Example 2: Verification on Effect of pCK-HGFX7 on Cell Growth after ENC Maturation The effect of pCK-HGFX7 on cell growth after ENC maturation was verified. To this end, $5 \times 10^4$ ENCs were seeded, followed by maturation for 6 days. After 6 days, the cells were treated with 1.25 ng/ml of the protein obtained from 293F cells transfected with pCK-HGFX7, thereby verifying the effect of pCK-HGFX7 on cell growth. After 3 days of the treatment with pCK-HGFX7, an MTT assay was carried out to measure the cell growth.

Figure 2:
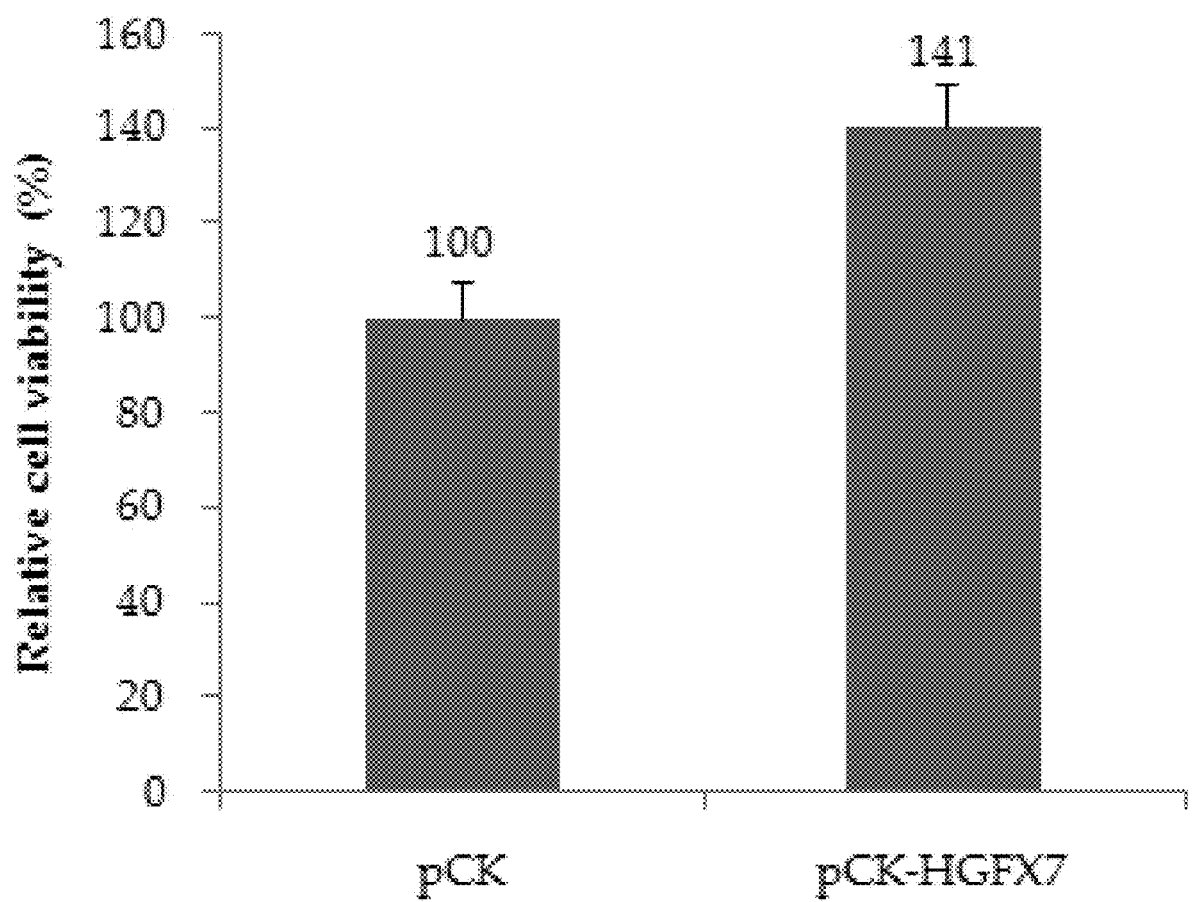
FIG. 2 depicts an effect of pCK-HGFX7 on the growth of ENC cells according to an embodiment of the present invention.

The results confirmed that, as shown in FIG. 2, the cell growth was significantly increased by about 40% in the pCK-HGFX7 treatment group rather than the pCK treatment group as a control.

Example 3: Verification on Effect of pCK-HGFX7 on Cell Growth and Apoptosis in Mouse Motor Neuronal Cells (NSC-34)

3-1. Cell Line and Cell Culture

NSC-34 cells (Cellution Biosystem, Vancouver, Calif.) used in the present test are mouse-derived motor neuronal cells. NSC-34 cells correspond to a cell line in which motor neuronal cells derived from the spinal nerve of the embryonic mouse are mixed with neuroblastoma cells, and are widely used in studies associated with the motor nerve. The cells were cultured in Dulbecco's modified Eagle's medium (DMEM, Sigma) supplemented with 10% bovine fetal serum and an antibiotic material (Gibco BRL, USA) under the conditions of 37° C. and 5% $CO_2$. The medium, reagent, and serum for cell culture were purchased from Gibco and Sigma aldrich.

3-2. Production and Quantification of Supernatant Expressing HGF Protein

DNA transfection was used to produce the supernatant expressing HGF protein. The transfection was carried out using the FuGene HD transfection system (Promega, USA) according to the manufacturer's protocol. 293T cells were seeded at $1 \times 10^6$ cells, and the next day, the cells were transfected with 3 µg of pCK, pCK-HGF728 (pCK-cHGF in PCT/KR03/000548), pCK-HGF723 (pCK-dHGF in PCT/KR03/000548), and pCK-HGFX7 DNA. After culture for 48 h, respective supernatants were all harvested, and then filtered through a 0.22-µm filter. The expression level of the HGF protein contained in each supernatant was measured using human HGF immunoassay. Each supernatant was again diluted to 1 µg/ml for the use of tests. Recombinant human HGF protein used in the human HGF immunoassay was purchased from R&D (R&D Systems, Inc., MSP, USA) for use.

3-3. Effect of Human pCK-HGFX7 on Cell Growth in NSC-34 Cells

In order to verify the effect of pCK-HGFX7 on the growth of motor neuronal cells, NSC-34 cells were treated with pCK-HGFX7, and then the degree of cell proliferation was evaluated. The cells were cultured in a culture medium supplemented with 10% bovine fetal serum, and then, for the use for tests, the culture was suspended using Dulbecco's modified Eagle's medium (DMEM, Sigma) supplemented with 1% bovine fetal serum. The cells were seeded in a 6-well plate such that $3 \times 10^4$ of the cells were contained in 2 ml of a medium containing 1% serum. After 2 h of the seeding, respective supernatants obtained from 293T cells transfected with pCK-HGF728, pCK-HGF723, and pCK-HGFX7 were added to a 6-well plate at 100 uL per well such that the concentration of the HGF protein is 50 ng/ml. The supernatant obtained by transfecting 293T cells with pCK vector was used as a control. After 48 h of culturing, the media in the 6-well plate were exchanged. After 2 ml of a medium containing 1% bovine fetal serum was added to each well, each of the supernatants obtained from 293T cells transfected with pCK-HGF728, pCK-HGF723, and pCK-HGFX7 was added such that the concentration of the HGF protein is 50 ng/ml, followed by culturing for 48 h. The supernatant obtained by transfecting 293T cells with pCK vector was used as a control. The cultured cells were collected and counted. The pCK vector was used for a control.

As a result of culturing for 5 days after cell seeding, when the groups treated with respective supernatants obtained from 293T cells transfected with pCK, pCK-HGF728, pCK-HGF723, and pCK-HGFX7 were compared with the pCK treatment group, the cell proliferation was induced by about 20% in the pCK-HGF728 or pCK-HGF723 treatment group and the cell growth was increased by about 48% in the pCK-HGFX7 treatment group. Through these results, it could be verified that pCK-HGFX7 can significantly increase the cell growth of motor neuronal cells compared with pCK-HGF728 or pCK-HGF723.

3-4. Effect of pCK-HGFX7 on Apoptosis in NSC-34 Cells

NSC-34 cells were suspended at $3 \times 10^4$ in Dulbecco's modified Eagle's medium supplemented with 1% bovine fetal serum, and then seeded in a 6-well plate. After the seeding of cells, the cells were stabilized for 2 h, and then each of the supernatants obtained from 293T cells transfected with pCK-HGF728, pCK-HGF723, and pCK-HGFX7 was added such that the concentration of HGF protein was 50 ng/ml. The supernatant obtained by transfecting 293T cells with pCK vector was used as a control. The cells were cultured for 5 days while the medium and each of the supernatants were exchanged at intervals of 2-3 days.

RNA was extracted from the cells, which were cultured for 5 days, using Trizol reagent (Life technologies, USA), and the extracted RNA was used to synthesize cDNA using First Strand cDNA Kit (Roche, USA). Real-time polymerase chain reaction (PCR) was conducted using the synthesized cDNA as a template and the nucleotides of SEQ ID NOs: 11 and 12 for Bax gene or the nucleotides of SEQ ID NOs: 13 and 14 for Bcl-12 gene as primers. Real-time PCR was performed by mixing 1 µl of the template cDNA, 1 µl of 10 pmol/µl primers each, 12.5 µl of SYBR green PCR master mix (Life technologies, USA), and 9.5 µl of sterilized tertiary distilled water to prepare a total of 25 µl of a mixture liquid and then conducting a reaction under conditions of 2 min at 50° C. and 10 min at 95° C., and then 40 cycles of 15 s at 95° C. and 1 min at 60° C. Here, in order to correct each reaction value, real-time PCR was performed using, as primers, the nucleotides of SEQ ID NOs: 15 and 16 for GAPDH as a housekeeping gene. As test results, the expression of the Bax gene associated with apoptosis was reduced in each of HGF supernatant treatment groups rather than the pCK treatment group, and especially, the expression of Bcl-2 associated with anti-apoptosis was increased by 1.3-fold in the pCK-HGFX7 treatment group rather than the pCK treatment group (see FIG. 4a). Through this test, it was confirmed that, in the medium containing 1% bovine fetal serum, pCK-HGFX7 inhibited apoptosis by about 40%, compared with the pCK treatment group as a control (see FIG. 4b).

Example 4: Verification on Effect of pCK-HGFX7 on Survival of NSC-34 Cells Under Oxidative Stress Culture Conditions 4-1. Selection of Concentration of Hydrogen Peroxide Solution Inducing NSC-34 Cell Apoptosis by Oxidative Stress Prior to verification of the effect of pCK-HGFX7 on NSC-34 cell apoptosis induced by hydrogen peroxide solution, the cell seeding concentration that is suitable to validate NSC-34 cell apoptosis, and the concentration of hydrogen peroxide solution for inducing apoptosis were selected.

The cells cultured in a culture medium supplemented with 10% bovine fetal serum were collected, and then suspended in Dulbecco's modified Eagle's medium supplemented with 1% bovine fetal serum, followed by cell counting. The counted cells were seeded in a 96-well plate at a cell concentration of $1\times10^4$, and then treated the next day with 10, 20, 30, 50, and 100 µM hydrogen peroxide solutions. The phosphate buffered saline was added to a well that was not treated with hydrogen peroxide solution, and the well was used as a control. After 24 h, the degree of apoptosis was measured using the XTT test method (Roche, USA). It was verified that the test groups treated with different concentrations of hydrogen peroxide solution induced 0, 10, 30, 70, and 85% apoptosis compared with the control. Based on these results, the suitable concentration of hydrogen peroxide solution for inducing NSC-34 cell apoptosis was selected to 30 µM.

Additionally, in order to carry out the apoptosis test in a 6-well plate, the cells were seeded in the 6-well plate such that the cells were contained at $1.5\times10^5$, $3\times10^5$, and $1\times10^6$ in 2 ml of media containing 1% bovine fetal serum. The next day, NSC-34 cells were treated with the 30 µM hydrogen peroxide solution, and the cell count was carried out on day 1, 4, and 7. As a result of confirming the cell count on day 7, the cells in the well in which $1.5\times10^5$ cells were seeded were all dead, and thus cannot be selected for the test, and the apoptosis was not induced in the well in which $1\times10^6$ cells were seeded. Based on these test results, the cell count and the concentration of hydrogen peroxide solution in the test for apoptosis induction were selected to $3\times10^5$ and 30 µM, respectively.

4-2. Verification on Effect of pCK-HGFX7 on Survival of NSC-34 Cells Under Oxidative Stress Culture Conditions NSC-34 cells were cultured in a culture medium supplemented with 10% bovine fetal serum, and, for the use for the apoptosis inhibition test, the culture was suspended using Dulbecco's modified Eagle's medium supplemented with 1% bovine fetal serum. The cells were seeded in a 6-well plate such that $3\times10^5$ of the cells were contained in 2 ml of a medium containing 1% serum. The next day, respective wells were treated with 30 µM hydrogen peroxide solution selected from the prior test, and then treated with respective supernatants obtained from 293T cells transfected with pCK-HGF728, pCK-HGF723, and pCK-HGFX7 such that the concentration of the HGF protein was 50 ng/ml. A culture medium obtained by transfecting cells with pCK vector was used as a control. While the cells were cultured for 7 days, the degree of apoptosis was observed. After 7 days of cell seeding, the cells were collected and counted. As a result of cell counting, it was verified that, only about 60-70% of cells survived as compared with the originally seeded cells in the test groups treated with pCK, pCK-HGF728, and pCK-HGF723, whereas NSC-34 cells treated with pCK-HGFX7 showed about 92% survival, indicating the excellent apoptosis inhibition compared with the groups treated with the other test materials. These results confirmed that the HGFX7 protein effectively inhibited motor neuron apoptosis induced by oxidative stress due to the hydrogen peroxide solution (see FIG. 5).

4-3. Verification on Effect of pCK-HGFX7 on NSC-34 Cell Apoptosis Under Oxidative Stress Culture Conditions NSC-34 cells were suspended at $3\times10^5$ in Dulbecco's modified Eagle's medium supplemented with 1% bovine fetal serum, and then seeded in a 6-well plate. The next day, respective wells were treated with 30 µM hydrogen peroxide solution, and then treated with respective supernatants obtained from 293T cells that were transfected with pCK-HGF728, pCK-HGF723, and pCK-HGFX7 such that the concentration of the HGF protein was 50 ng/ml, followed by culturing for 7 days. The supernatant obtained by transfecting cells with pCK vector was used as a control.

RNA was extracted from the cells, which were cultured for 7 days, using the Trizol reagent, and the extracted RNA was used to synthesize cDNA using the First Strand cDNA Kit. Real-time polymerase chain reaction (PCR) was conducted using the synthesized cDNA as a template and the nucleotides of SEQ ID NOs: 11 and 12 for Bax gene or the nucleotides of SEQ ID NOs: 13 and 14 for Bcl-12 gene as primers. Real-time PCR was performed by mixing 1 µl of the template cDNA, 1 µl of 10 pmol/µl primers each, 12.5 µl of SYBR green PCR master mix (Life technologies, USA), and 9.5 µl of sterilized tertiary distilled water to prepare a total of 25 µl of a mixture liquid and then conducting a reaction under conditions of for 2 min at 50° C. and 10 min at 95° C., and then 40 cycles of 15 s at 95° C. and 1 min at 60° C. Here, in order to correct each reaction value, real-time PCR was performed using, as primers, the nucleotides of SEQ ID NOs: 15 and 16 for GAPDH as a housekeeping gene. The test results confirmed that the expression of the Bax gene associated with apoptosis induction was reduced and the expression of Bcl-2 associated with anti-apoptosis was increased in each of HGF supernatant treatment groups rather than the pCK treatment group. Especially, the expression of Bax gene was reduced by about 70% (see FIG. 6a), and the Bax/Bcl-2 ratio was decreased by about 75%, indicating an excellent apoptotic effect (see FIG. 6b), in the pCK-HGFX7 treatment group rather than the pCK treatment group.

Example 5: Verification on Effect of pCK-HGFX7 on Cell Growth in G93A Mutant hSOD1-Delivered Cells The in vitro assay using the G93A mutant form of superoxide dismutase 1 (SOD1), which is one of the ALS causes, has been developed by many researchers. Especially, it has been reported that the delivery of the G93A mutant form of hSOD1 into NSC-34 cells, which have been widely used in the motor neuron research, can induce apoptosis (Cheema et al., 2005). Therefore, in the present test, pCK-hSOD1-wild type and pCK-hSOD1-G93A were manufactured by inserting human SOD1 wild type gene (wild type; WT) (NM_000454) and the human SOD1 gene, in which the 93rd amino acid residue was substituted from glycine to alanine, into the BamHI site of the pCK vector, respectively. The following test was carried out to investigate the effect of pCK-HGFX7 in NSC34 cells in which hSOD1-G93A was delivered using the prepared plasmid.

NSC-34 cells were seeded in a 96-well plate such that the cells were suspended at 1×10⁴ in Dulbecco's Modified Eagle's medium supplemented with 10% fetal bovine serum. The next day, the cells were transfected with pCK, pCK-hSOD1-wild type (WT), and pCK-hSOD1-G93A mutant (G93A) using the lipofectamin LTX reagent (Life technologies, USA). Immediately before the transfection, G93A-transfected cells were treated with the supernatants obtained from 293T cells that were transfected with pCK-HGF728 and pCK-HGFX7 such that the concentration of HGF protein was 50 ng/ml. The supernatant obtained by transfecting cells with pCK vector was used as a control.

After culturing for 3 days, the cell growth was confirmed through the treatment with the XTT reagent. The results confirmed that the wild type hSOD1-delivered cells and the pCK vector-delivered cells showed a similar cell growth. However, the G93A mutant hSOD1-delivered cells showed about 85.8% cell growth, compared with the pCK-delivered cells, showing the deterioration in cell growth compared with the wild type hSOD1-delivered cells. However, the pCK-HGFX7 treatment group shows about 92.9% cell growth, indicating the effect of inhibiting the deterioration in cell growth, which is caused by the delivery of G93A mutant hSOD1 (see FIG. 7).

```
[Gene sequences]
SEQ ID NO: 11: GGC AGA CAG TGA CCA TCT TT

SEQ ID NO: 12: AGT GGA CCT GAG GTT TAT TG

SEQ ID NO: 13: CCA TCA ATC AAA GCC AAG CA

SEQ ID NO: 14: AGC CTT CAC GCA AGT TCA GG

SEQ ID NO: 15: CCA TCA CTG CCA CTC AGA AGA C

SEQ ID NO: 16: TCA TAC TTG GCA GGT TTC TCC
```

Example 6: Verification of pCK-HGFX7 on Grip Strength in Human Mutant SOD1-G93A Tg Mouse (Hereinafter, ALS Mouse)

As superoxide dismutase 1 (SOD1) mutation has been found to be one of the ALS causes, the ALS mouse model using this gene was developed, and currently, ALS researchers throughout the world have conducted various researches using this animal model. Out of these, B65JL-Tg (SOD1*G93A)1Gur/J (002726), which has been widely used, was selected, and used for tests. The manufacture of the ALS mouse model was requested to Woo Jung BSC (Korea), and the mouse model was used for the present test after it was verified whether the mutant type SOD1 gene was expressed, through genotyping.

10-week aged ALS mice were divided into 4 mice per group: Tg-pCK, Tg-pCK-HGF728 (pCK-cHGF in PCT/KR03/00548), and Tg-pCK-HGFX7 administration groups. Six mice without Tg were selected and set as a negative control (hereinafter, non-Tg). After the two weeks, the mice of the three test groups, excluding the negative control, were administered with the corresponding plasmid via intramuscular injection. Herein, 50 μl of the corresponding plasmid was administered at 2 μg/μl to arm triceps muscle, tibial muscle, musculus rectus femoris, and gastrocnemius muscle in left and right, respectively. After two weeks of the administration (14 week age), the grip strength of each mouse was investigated through the behavior test. For the behavior test, the mesh grip strength test was conducted. The mesh grip strength test was used to assess grip strength by placing a mouse on a wire net having lattices at predetermined intervals, overturning the wire net, and then measuring the time while the mouse is suspended from the wire net. This is one of the representative methods for assessing muscular strength of the mouse (Crawley J N, 2008).

As a test result, the non-Tg mice were overturned for an average of about 9 min, but, out of Tg individuals, the mice receiving pCK were suspended and overturned for an average of about 30 s. The individual receiving pCK-HGF728 plasmid showed a slight increased average duration time compared with pCK administration group, and the duration was an average of 49 s. Whereas, the mice receiving pCK-HGFX7 were suspended and overturned for a longer time compared with the mice receiving pCK or pCK-HGF728, and the average duration time was 3 min (see FIG. 8). This shows that pCK-HGFX7 significantly improved the muscular function, including the grip strength, of ALS mice compared with pCK and pCK-HGF728.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating amyotrophic lateral sclerosis, the method comprising administering, to a human patient with amyotrophic lateral sclerosis, a composition containing, as an active ingredient, a polynucleotide encoding two or more isoforms of hepatocyte growth factor (HGF), wherein:
the two or more isoforms of HGF comprise a full-length HGF (flHGF) and a deleted variant HGF (dHGF),
the full-length HGF (flHGF) comprises an amino acid sequence of SEQ ID NO:1, and the deleted variant HGF (dHGF) comprises the amino acid sequence of SEQ ID NO: 2.

2. The method of claim 1, wherein the polynucleotide is naked DNA, or is contained in a gene delivery system.

3. The method of claim 2, wherein the gene delivery system is a vector.

4. The method of claim 3, wherein the vector is a plasmid.

5. The method of claim 4, wherein the vector is pCK.

6. The method of claim 1, wherein the polynucleotide includes a sequence corresponding to exon 1 to exon 18 of a human HGF gene, and intron 4 of a human HGF gene or a fragment thereof as a sequence additionally inserted between exon 4 and exon 5.

7. The method of claim 6, wherein the polynucleotide includes a nucleotide sequence selected from the group consisting of SEQ ID NO: 3 to SEQ ID NO: 10.

8. The method of claim 7, wherein the polynucleotide includes a nucleotide sequence of SEQ ID NO: 9.

9. The method of claim 1, wherein the polynucleotide is administered at a dose of 1 µg to 2500 mg.

10. A method for treating amyotrophic lateral sclerosis comprising the step of administering, to a human patient with amyotrophic lateral sclerosis, a polynucleotide, wherein the polynucleotide comprises:
(a) a first cDNA which has the same sequence as exons 1-4 of a human HGF gene wherein said exons 1-4 are arranged in sequential order without an intron therebetween, or degenerates thereof which do not alter the amino acid sequence encoded by said first cDNA,
(b) a polynucleotide that has the same sequence as intron 4 of the human HGF gene or a fragment thereof, and
(c) a second cDNA which has the same sequence as exons 5-18 of the human HGF gene wherein said exons 5-18 are arranged in sequential order without an intron therebetween, or degenerates thereof which do not alter the amino acid sequence encoded by said second cDNA;
wherein (b) is located between (a) and (c); and the polynucleotide simultaneously encodes two heterotypes of human HGF.

11. A method for treating amyotrophic lateral sclerosis comprising the step of: intramuscular administration of pCK-HGFX7 to a human patient with amyotrophic lateral sclerosis.

* * * * *

UNITED STATES PATENT AND TRADEMARK OFFICE
CERTIFICATE OF CORRECTION

| | | |
|---|---|---|
| PATENT NO. | : 10,639,351 B2 | Page 1 of 1 |
| APPLICATION NO. | : 15/030999 | |
| DATED | : May 5, 2020 | |
| INVENTOR(S) | : Jae Gyun Jeong | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 420 days.

Signed and Sealed this
Twenty-fourth Day of November, 2020

Andrei Iancu
*Director of the United States Patent and Trademark Office*